(12) United States Patent
Takahashi

(10) Patent No.: US 11,649,474 B2
(45) Date of Patent: May 16, 2023

(54) METHOD FOR PRODUCING GLYCOPROTEIN HAVING MANNOSE RESIDUE AS NON-REDUCING END OF SUGAR CHAIN

(71) Applicant: JCR Pharmaceuticals Co., Ltd., Hyogo (JP)

(72) Inventor: Kenichi Takahashi, Hyogo (JP)

(73) Assignee: JCR Pharmaceuticals Co., Ltd., Hyogo (JP)

( * ) Notice: Subject to any disclaimer, the term of this patent is extended or adjusted under 35 U.S.C. 154(b) by 1107 days.

(21) Appl. No.: 16/292,952

(22) Filed: Mar. 5, 2019

(65) Prior Publication Data

US 2019/0256883 A1 Aug. 22, 2019

Related U.S. Application Data

(63) Continuation of application No. 13/879,037, filed as application No. PCT/JP2011/073589 on Oct. 13, 2011, now abandoned.

(30) Foreign Application Priority Data

Oct. 15, 2010 (JP) ................................ 2010-232893

(51) Int. Cl.
 *C12P 21/00* (2006.01)
 *C12N 9/24* (2006.01)
(52) U.S. Cl.
 CPC .......... *C12P 21/005* (2013.01); *C12N 9/2402* (2013.01); *C12Y 302/01052* (2013.01); *C12Y 302/01096* (2013.01)
(58) Field of Classification Search
 None
 See application file for complete search history.

(56) References Cited

U.S. PATENT DOCUMENTS

| | | | |
|---|---|---|---|
| 5,236,838 A | 8/1993 | Rasmussen et al. | |
| 5,272,063 A | 12/1993 | Chan | |
| 7,214,514 B2 | 5/2007 | Brandt | |
| 7,214,532 B2 | 5/2007 | Stern | |
| 7,659,373 B2 | 2/2010 | Burg | |
| 2002/0142386 A1 | 10/2002 | Betenbaugh | |
| 2005/0032211 A1 | 2/2005 | Shaaltiel | |
| 2006/0204487 A1 | 9/2006 | Shaaltiel et al. | |
| 2008/0038232 A1 | 2/2008 | Shaaltiel et al. | |
| 2009/0053762 A1 | 2/2009 | Shaaltiel | |
| 2009/0208477 A1 | 8/2009 | Shaaltiel et al. | |
| 2010/0136673 A1 | 6/2010 | Shaaltiel | |
| 2010/0196345 A1 | 8/2010 | Shaaltiel et al. | |
| 2011/0203009 A1 | 8/2011 | Tomita | |

FOREIGN PATENT DOCUMENTS

| | | |
|---|---|---|
| JP | H08-027181 A | 1/1996 |
| JP | 2003002899 A | 1/2003 |
| JP | 2006524506 A | 11/2006 |
| JP | 2009254324 A | 11/2009 |
| WO | 9928455 A1 | 6/1999 |
| WO | 2002015927 A1 | 2/2002 |
| WO | 2004096978 A2 | 11/2004 |
| WO | 2005066339 A2 | 7/2005 |
| WO | 2009079376 A2 | 6/2009 |
| WO | 2009127826 A1 | 10/2009 |
| WO | 2010015722 A1 | 2/2010 |

OTHER PUBLICATIONS

Hossler et al., "Optimal and consistent protein glycosylation in mammalian cell culture", 19(9), Glycobiology, 936-949, (2009).
Nomura T. Et al., J Biosci Bioeng. (2010) vol. 110, No. 4, pp. 386-391.
Altmann F: Journal of Biological Chemistry, vol. 270 No. 29, pp. 17344-17349(1995).
Watanabe S :Journal of Biological Chemistry, vol. 277 No. 7; pp. 5090-5093(2002).
Van Patten SM: Glycobiology.vol. 17. No. 5; pp. 467-478(2007).
Ripka J.J Cell Biochem.vol. 42. pp. 117-122(1990).
Cerezyme Injection 200U (2010 package insert-genzymeTM) (pp. 1-2) and English translation thereof.
Sato Y: Journal of Clinical Investigation; vol. 91.pp. 1909-1919(May 1993).
Christoph Geisler: Identification of genes encoding N-glycan processing β-N-acetylglucosaminidases in Trichoplusia ni and Bombyx mori: Implications for glycoengineering of baculovirus expression systems; Biotechnology Progress; vol. 26, Issue1 pp. 34-44 (2009).
Christoph Geisler: A fused lobes Gene Encodes the Processing β-N-Acetylglucosaminidase in Sf9 Cells; The Journal of Biological Chemistry, 283, 11330-11339 (2008).
International Search Report from PCT/JP2011/073589 dated Jan. 17, 2012.
L. Wells et al. "Dynamic O-glycosylation of nuclear and cytosolic proteins: further characterization of the nucleocytoplasmic beta-N-acetylglucosaminidase, O-GlcNAcase" Journal Biol. Chem. [Jan. 18, 2002], vol. 277(3), pp. 1755-1761.
E. Chitlaru et al. "Molecular cloning and characterization of a novel beta-N-acetyl-D-glucosaminidase from Vibrio furnissii" Journal Biol. Chem. [Dec. 27, 1996], vol. 271(52), pp. 33433-33439.
J.J. Aumiller et al. "Molecular cloning and functional characterization of beta-N-acetylglucosaminidase genes from Sf9 cells" Protein Expr. Purif. [Jun. 2006], vol. 47(2), pp. 571-590.

(Continued)

*Primary Examiner* — Nancy J Leith
(74) *Attorney, Agent, or Firm* — Millen, White, Zelano & Branigan, PC; Ryan Pool

(57) ABSTRACT

Disclosed is a method for producing a glycoprotein using mammalian cells, wherein all or part of the non-reducing ends of N-glycoside binding sugar chains are mannose residues. The method is a method for producing glycoproteins using transformant mammalian cells which are prepared by introducing thereinto a β-N-acetylglucosaminidase gene and inducing its expression.

14 Claims, 8 Drawing Sheets

Specification includes a Sequence Listing.

(56) References Cited

OTHER PUBLICATIONS

N. Tomiya et al. "Comparing N-glycan processing in mammalian cell lines to native and engineered lepidopteran insect cell lines" Glycoconj J. [2004], vol. 21(6), pp. 343-360.

```
                              SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Primer Hyg-Sfi

<400> SEQUENCE: 1
gaggccgcct cggcctctga                                                  20

<210> SEQ ID NO 2
<211> LENGTH: 29
<212> TYPE: DNA
<213> ORGANISM: Artificial Sequence
<220> FEATURE:
<223> OTHER INFORMATION: Primer Hyg-BstX

<400> SEQUENCE: 2
aaccatcgtg atgggtgcta ttcctttgc                                        29

<210> SEQ ID NO 3
<211> LENGTH: 47
<212> TYPE: DNA
<213> ORGANISM: Artificial Sequence
<220> FEATURE:
<223> OTHER INFORMATION: Primer GBA-Mlu

<400> SEQUENCE: 3
gcaatacgcg tccgccacca tggagttttc aagtccttcc agagagg                    47

<210> SEQ ID NO 4
<211> LENGTH: 41
<212> TYPE: DNA
<213> ORGANISM: Artificial Sequence
<220> FEATURE:
<223> OTHER INFORMATION: Primer GBA-Not

<400> SEQUENCE: 4
ggacgcggcc gcgagctctc actggcgacg ccacaggtag g                          41

<210> SEQ ID NO 5
<211> LENGTH: 38
<212> TYPE: DNA
```

<213> ORGANISM: Artificial Sequence
<220> FEATURE:
<223> OTHER INFORMATION: Primer N-AGase5'-Sal

<400> SEQUENCE: 5
ccggtcgacc atgttacggc acgtaatatt gttattcg                          38

<210> SEQ ID NO 6
<211> LENGTH: 21
<212> TYPE: DNA
<213> ORGANISM: Artificial Sequence
<220> FEATURE:
<223> OTHER INFORMATION: Primer N-AGase5'-Mlu

<400> SEQUENCE: 6
accaatcagt ttataggtga t                                            21

<210> SEQ ID NO 7
<211> LENGTH: 20
<212> TYPE: DNA
<213> ORGANISM: Artificial Sequence
<220> FEATURE:
<223> OTHER INFORMATION: Primer N-AGase3'-Mlu

<400> SEQUENCE: 7
gaagtacacc cacagaggtc                                              20

<210> SEQ ID NO 8
<211> LENGTH: 42
<212> TYPE: DNA
<213> ORGANISM: Artificial Sequence
<220> FEATURE:
<223> OTHER INFORMATION: Primer N-AGase3'-Not

<400> SEQUENCE: 8
gcttgcggcc gcctaaaagt aattccctgt tacgcaaaat cc                     42

<210> SEQ ID NO 9
<211> LENGTH: 1917
<212> TYPE: DNA
<213> ORGANISM: Artificial Sequence
<220> FEATURE:
<223> OTHER INFORMATION: Artificial Sequence containing SfFDL CDS, bases
      1-6: MluI site, bases 14-1909: CDS for SfFDL, bases 1910-1917:
      NotI site
<220> FEATURE:
<221> NAME/KEY: CDS
<222> LOCATION: (14)..(1909)
<223> OTHER INFORMATION: SfFDL

<400> SEQUENCE: 9
acgcgtcgcc acc atg aag tgg tgg ggc gag gga ctg ggt cgc ggc gcc      49
            Met Lys Trp Trp Gly Glu Gly Leu Gly Arg Gly Ala
            1               5                   10 agc gcc cag ctg agc cgc gtg gcc cga atg cgg cgc gct ctt ctc ctg     97
Ser Ala Gln Leu Ser Arg Val Ala Arg Met Arg Arg Ala Leu Leu Leu
        15                  20                  25 ctc gcc gct gcc gca tgc acc gcg gca gct ctg ctg tac tgg cgc cag    145
Leu Ala Ala Ala Ala Cys Thr Ala Ala Ala Leu Leu Tyr Trp Arg Gln
 30                  35                  40 cag agc gac gac cgc gcc cac cgc cct ctg cat gcc ctc tac gag ggc    193
Gln Ser Asp Asp Arg Ala His Arg Pro Leu His Ala Leu Tyr Glu Gly
 45                  50                  55                  60 gtg gag ccc cag tgg agc tgg gtg tgc cgc aac ctg cgc tgc gag cgc    241
Val Glu Pro Gln Trp Ser Trp Val Cys Arg Asn Leu Arg Cys Glu Arg
             65                  70                  75

```
ctc ctg gca acc gag acc acc acc ctg cag agc ctg ccc acc tgc aat       289
Leu Leu Ala Thr Glu Thr Thr Thr Leu Gln Ser Leu Pro Thr Cys Asn
            80              85                  90 atg ctt tgc gac agc acc cag ctg tgg ccc cag ccc acc ggc gcc gtg       337
Met Leu Cys Asp Ser Thr Gln Leu Trp Pro Gln Pro Thr Gly Ala Val
        95                  100                 105 agc ctg gcc acc gcc gtg cag ccc gtg cgc gca gag gga ttc aag ctg       385
Ser Leu Ala Thr Ala Val Gln Pro Val Arg Ala Glu Gly Phe Lys Leu
    110                 115                 120 cag atc gtg acc agc ccc agc cgc gac gtg agc gac cac ctg gcc gac       433
Gln Ile Val Thr Ser Pro Ser Arg Asp Val Ser Asp His Leu Ala Asp
125             130                 135                 140 gcc ttc gag ctg atg aag gag gac atg cgc acc ctg gag cgc agc gcc       481
Ala Phe Glu Leu Met Lys Glu Asp Met Arg Thr Leu Glu Arg Ser Ala
                145                 150                 155 ggc agc gag cgc cgc ccc gcc gac tac ggc ctg ccc cgc aac gtg ctg       529
Gly Ser Glu Arg Arg Pro Ala Asp Tyr Gly Leu Pro Arg Asn Val Leu
            160                 165                 170 gtg cgc gtg gcc atc aac ggc agc gcc gac ccc cgc atg cgg ctg gat       577
Val Arg Val Ala Ile Asn Gly Ser Ala Asp Pro Arg Met Arg Leu Asp
        175                 180                 185 acc gac gag agc tac aag ctg acc ctg cgc ccc agc cgc aag agc ctg       625
Thr Asp Glu Ser Tyr Lys Leu Thr Leu Arg Pro Ser Arg Lys Ser Leu
    190                 195                 200 gtg gcc gac atc acc gcc cac agc ttc tgc ggc gcc cgc cac ggc ctg       673
Val Ala Asp Ile Thr Ala His Ser Phe Cys Gly Ala Arg His Gly Leu
205             210                 215                 220 gag acc ctg agc cag atc gtg tgg atg gac ccc tac gcc ggc tgc ctg       721
Glu Thr Leu Ser Gln Ile Val Trp Met Asp Pro Tyr Ala Gly Cys Leu
                225                 230                 235 ctg atc ctg gag gcc gcc acc gtg gtg gac gcc ccc cgc ttc ccc tac       769
Leu Ile Leu Glu Ala Ala Thr Val Val Asp Ala Pro Arg Phe Pro Tyr
            240                 245                 250 cgc ggc ctg ctg ctg gac acc gcc cgc aac ttc ttc ccc acc ggc gag       817
Arg Gly Leu Leu Leu Asp Thr Ala Arg Asn Phe Phe Pro Thr Gly Glu
        255                 260                 265 atc ctg cgc acc atc gac gcc atg gcc gcc agc aag atg aac acc ttc       865
Ile Leu Arg Thr Ile Asp Ala Met Ala Ala Ser Lys Met Asn Thr Phe
    270                 275                 280 cac tgg cac gtg agc gac agc cag agc ttc ccc ctg cga ctg gat agc       913
His Trp His Val Ser Asp Ser Gln Ser Phe Pro Leu Arg Leu Asp Ser
285             290                 295                 300 gcc ccc cag ctg gcc cag cat gga gcc tac ggc ccc ggc gcc gtg tac       961
Ala Pro Gln Leu Ala Gln His Gly Ala Tyr Gly Pro Gly Ala Val Tyr
                305                 310                 315 acc agc gac gac gtg aag acc atc gtg cgc cac gcc aag ctg cgc ggc      1009
Thr Ser Asp Asp Val Lys Thr Ile Val Arg His Ala Lys Leu Arg Gly
            320                 325                 330 atc cgc gtg ctg ctg gag gtg gac gcc ccc gcc cac gtg ggc cgc gcc      1057
Ile Arg Val Leu Leu Glu Val Asp Ala Pro Ala His Val Gly Arg Ala
        335                 340                 345 tgg ggc tgg ggc ccc agc gcc ggc ctg ggc cac ctg gcc cac tgc gtg      1105
Trp Gly Trp Gly Pro Ser Ala Gly Leu Gly His Leu Ala His Cys Val
    350                 355                 360 gag ctg gag ccc tgg agc gcc tac tgc ggc gag ccc ccc tgc ggc cag      1153
Glu Leu Glu Pro Trp Ser Ala Tyr Cys Gly Glu Pro Pro Cys Gly Gln
365                 370                 375                 380 ctg aac ccc cgc aac ccc cac gtg tac gac ctg ctg cag cgc atc tac      1201
Leu Asn Pro Arg Asn Pro His Val Tyr Asp Leu Leu Gln Arg Ile Tyr
```

-continued

```
                        385                 390                 395
gcc gag atc ctg gcc ctg acc gag gtg gac gac gtg ttc cac ctg ggc      1249
Ala Glu Ile Leu Ala Leu Thr Glu Val Asp Asp Val Phe His Leu Gly
            400                 405                 410 ggc gac gag gtg agc gag cgc tgc tgg gcc cag cac ttc aac gac acc      1297
Gly Asp Glu Val Ser Glu Arg Cys Trp Ala Gln His Phe Asn Asp Thr
        415                 420                 425 gac ccc atg gac ctg tgg ctg gag ttc acc cgc cgc gcc ctg cat gca      1345
Asp Pro Met Asp Leu Trp Leu Glu Phe Thr Arg Arg Ala Leu His Ala
    430                 435                 440 ctg gag cgc gcc aac ggc ggc aag ctg ccc gag ctg gtg ctg ctg tgg      1393
Leu Glu Arg Ala Asn Gly Gly Lys Leu Pro Glu Leu Val Leu Leu Trp
445                 450                 455                 460 agc agc cgc ctg acc cgc agc ccc tac ctg gag cgc ctg gac agc cgc      1441
Ser Ser Arg Leu Thr Arg Ser Pro Tyr Leu Glu Arg Leu Asp Ser Arg
                465                 470                 475 cac ctg ggc gtg cag gtg tgg ggc agc agc cgc tgg ccc gag agc cgc      1489
His Leu Gly Val Gln Val Trp Gly Ser Ser Arg Trp Pro Glu Ser Arg
            480                 485                 490 gcc gtg ctg gac gcc ggc ttc cgc agc gtg ctg agc cac gtg gac gcc      1537
Ala Val Leu Asp Ala Gly Phe Arg Ser Val Leu Ser His Val Asp Ala
        495                 500                 505 tgg tac ctg gac tgc ggc ttc ggc agc tgg cgc gac agc agc gac ggc      1585
Trp Tyr Leu Asp Cys Gly Phe Gly Ser Trp Arg Asp Ser Ser Asp Gly
    510                 515                 520 cac tgc ggc ccc tac cgc agc tgg cag cag gtg tac gag cac cgc ccc      1633
His Cys Gly Pro Tyr Arg Ser Trp Gln Gln Val Tyr Glu His Arg Pro
525                 530                 535                 540 tgg acc gag gag gga ggt ggg gca gct gcc tgg cgc gtg gag ggc ggc      1681
Trp Thr Glu Glu Gly Gly Gly Ala Ala Ala Trp Arg Val Glu Gly Gly
                545                 550                 555 gcc gcc tgc cag tgg acc gag cag ctg gcc gcc ggc ggc ctg gac gcc      1729
Ala Ala Cys Gln Trp Thr Glu Gln Leu Ala Ala Gly Gly Leu Asp Ala
            560                 565                 570 cgc gtg tgg ccc cgc gca gcg gct ctg gcc gag cgc ctg tgg agc gac      1777
Arg Val Trp Pro Arg Ala Ala Ala Leu Ala Glu Arg Leu Trp Ser Asp
        575                 580                 585 cgc gcc gag ggc gcc ctg ccc gac gtg tac ctg cgc ctg gac acc cag      1825
Arg Ala Glu Gly Ala Leu Pro Asp Val Tyr Leu Arg Leu Asp Thr Gln
    590                 595                 600 cgc gcc cgc ctg ctg gcc cgc ggc gtg cgc gcc gcc ccc ctg tgg ccc      1873
Arg Ala Arg Leu Leu Ala Arg Gly Val Arg Ala Ala Pro Leu Trp Pro
605                 610                 615                 620 cgc tgg tgc agc cac aac ccc cac gcc tgc ctg tag gcggccgc             1917
Arg Trp Cys Ser His Asn Pro His Ala Cys Leu
                625                 630
```

<210> SEQ ID NO 10
<211> LENGTH: 631
<212> TYPE: PRT
<213> ORGANISM: Artificial Sequence
<220> FEATURE:
<223> OTHER INFORMATION: Synthetic Construct

<400> SEQUENCE: 10

```
Met Lys Trp Trp Gly Glu Gly Leu Gly Arg Gly Ala Ser Ala Gln Leu
1               5                   10                  15

Ser Arg Val Ala Arg Met Arg Arg Ala Leu Leu Leu Leu Ala Ala Ala
            20                  25                  30

Ala Cys Thr Ala Ala Ala Leu Leu Tyr Trp Arg Gln Gln Ser Asp Asp
```

```
            35                  40                  45
Arg Ala His Arg Pro Leu His Ala Leu Tyr Glu Gly Val Glu Pro Gln
 50                  55                  60

Trp Ser Trp Val Cys Arg Asn Leu Arg Cys Glu Arg Leu Leu Ala Thr
 65                  70                  75                  80

Glu Thr Thr Thr Leu Gln Ser Leu Pro Thr Cys Asn Met Leu Cys Asp
                     85                  90                  95

Ser Thr Gln Leu Trp Pro Gln Pro Thr Gly Ala Val Ser Leu Ala Thr
                    100                 105                 110

Ala Val Gln Pro Val Arg Ala Glu Gly Phe Lys Leu Gln Ile Val Thr
                115                 120                 125

Ser Pro Ser Arg Asp Val Ser Asp His Leu Ala Asp Ala Phe Glu Leu
            130                 135                 140

Met Lys Glu Asp Met Arg Thr Leu Glu Arg Ser Ala Gly Ser Glu Arg
145                 150                 155                 160

Arg Pro Ala Asp Tyr Gly Leu Pro Arg Asn Val Leu Val Arg Val Ala
                165                 170                 175

Ile Asn Gly Ser Ala Asp Pro Arg Met Arg Leu Asp Thr Asp Glu Ser
                180                 185                 190

Tyr Lys Leu Thr Leu Arg Pro Ser Arg Lys Ser Leu Val Ala Asp Ile
            195                 200                 205

Thr Ala His Ser Phe Cys Gly Ala Arg His Gly Leu Glu Thr Leu Ser
210                 215                 220

Gln Ile Val Trp Met Asp Pro Tyr Ala Gly Cys Leu Leu Ile Leu Glu
225                 230                 235                 240

Ala Ala Thr Val Val Asp Ala Pro Arg Phe Pro Tyr Arg Gly Leu Leu
                245                 250                 255

Leu Asp Thr Ala Arg Asn Phe Phe Pro Thr Gly Glu Ile Leu Arg Thr
            260                 265                 270

Ile Asp Ala Met Ala Ala Ser Lys Met Asn Thr Phe His Trp His Val
            275                 280                 285

Ser Asp Ser Gln Ser Phe Pro Leu Arg Leu Asp Ser Ala Pro Gln Leu
290                 295                 300

Ala Gln His Gly Ala Tyr Gly Pro Gly Ala Val Tyr Thr Ser Asp Asp
305                 310                 315                 320

Val Lys Thr Ile Val Arg His Ala Lys Leu Arg Gly Ile Arg Val Leu
                325                 330                 335

Leu Glu Val Asp Ala Pro Ala His Val Gly Arg Ala Trp Gly Trp Gly
            340                 345                 350

Pro Ser Ala Gly Leu Gly His Leu Ala His Cys Val Glu Leu Glu Pro
            355                 360                 365

Trp Ser Ala Tyr Cys Gly Glu Pro Pro Cys Gly Gln Leu Asn Pro Arg
            370                 375                 380

Asn Pro His Val Tyr Asp Leu Leu Gln Arg Ile Tyr Ala Glu Ile Leu
385                 390                 395                 400

Ala Leu Thr Glu Val Asp Asp Val Phe His Leu Gly Gly Asp Glu Val
                405                 410                 415

Ser Glu Arg Cys Trp Ala Gln His Phe Asn Asp Thr Asp Pro Met Asp
            420                 425                 430

Leu Trp Leu Glu Phe Thr Arg Arg Ala Leu His Ala Leu Glu Arg Ala
            435                 440                 445

Asn Gly Gly Lys Leu Pro Glu Leu Val Leu Leu Trp Ser Ser Arg Leu
450                 455                 460
```

```
Thr Arg Ser Pro Tyr Leu Glu Arg Leu Asp Ser Arg His Leu Gly Val
465                 470                 475                 480

Gln Val Trp Gly Ser Arg Trp Pro Glu Ser Arg Ala Val Leu Asp
                485                 490                 495

Ala Gly Phe Arg Ser Val Leu Ser His Val Asp Ala Trp Tyr Leu Asp
            500                 505                 510

Cys Gly Phe Gly Ser Trp Arg Asp Ser Ser Asp Gly His Cys Gly Pro
            515                 520                 525

Tyr Arg Ser Trp Gln Gln Val Tyr Glu His Arg Pro Trp Thr Glu Glu
            530                 535                 540

Gly Gly Gly Ala Ala Ala Trp Arg Val Glu Gly Gly Ala Ala Cys Gln
545                 550                 555                 560

Trp Thr Glu Gln Leu Ala Ala Gly Gly Leu Asp Ala Arg Val Trp Pro
                565                 570                 575

Arg Ala Ala Ala Leu Ala Glu Arg Leu Trp Ser Asp Arg Ala Glu Gly
            580                 585                 590

Ala Leu Pro Asp Val Tyr Leu Arg Leu Asp Thr Gln Arg Ala Arg Leu
            595                 600                 605

Leu Ala Arg Gly Val Arg Ala Ala Pro Leu Trp Pro Arg Trp Cys Ser
    610                 615                 620

His Asn Pro His Ala Cys Leu
625                 630

<210> SEQ ID NO 11
<211> LENGTH: 1917
<212> TYPE: DNA
<213> ORGANISM: Artificial Sequence
<220> FEATURE:
<223> OTHER INFORMATION: Artificial Sequence containing BmFDL CDS, bases
      1-6: MluI site, bases 14-1909 CDS for BmFDL, bases 1910-1917: NotI
      site
<220> FEATURE:
<221> NAME/KEY: CDS
<222> LOCATION: (14)..(1909)
<223> OTHER INFORMATION: BmFDL

<400> SEQUENCE: 11
acgcgtcgcc acc atg atg agc tgg ggc gac gcc ctg tgg ctg ggc ctg      49
           Met Met Ser Trp Gly Asp Ala Leu Trp Leu Gly Leu
           1               5                   10 acc gcc cgc ttc gcc cgc gtg ggc cgc ctg cgg cgc gct gtc ctg atg     97
Thr Ala Arg Phe Ala Arg Val Gly Arg Leu Arg Arg Ala Val Leu Met
        15                  20                  25 ctg gca gct gcg gcc tgc act gcc gct gcc gtt ctg tac tgg aag cag    145
Leu Ala Ala Ala Ala Cys Thr Ala Ala Ala Val Leu Tyr Trp Lys Gln
30                  35                  40 cag acc gac gac agc gcc aac cgc ccc ctg cat agt atg tac agc ggc    193
Gln Thr Asp Asp Ser Ala Asn Arg Pro Leu His Ser Met Tyr Ser Gly
45                  50                  55                  60 atc gag ccc cag tgg agc tgg ctg tgc cag cac gac cgc tgc gag cgc    241
Ile Glu Pro Gln Trp Ser Trp Leu Cys Gln His Asp Arg Cys Glu Arg
                65                  70                  75 tac cag gcc agc gac acc acc acc ctg cag agc ctg cag acc tgc aac    289
Tyr Gln Ala Ser Asp Thr Thr Thr Leu Gln Ser Leu Gln Thr Cys Asn
            80                  85                  90 atg ctg tgc gcc agc acc cag ctg tgg ccc cag ccc acc ggc ccc gtg    337
Met Leu Cys Ala Ser Thr Gln Leu Trp Pro Gln Pro Thr Gly Pro Val
        95                  100                 105 agc ctg gcc agc gcc gcc gtg ccc gtg cgc agc gac cgc ttc agc ctg    385
```

```
Ser Leu Ala Ser Ala Ala Val Pro Val Arg Ser Asp Arg Phe Ser Leu
    110                 115                 120 aag gtg atc gcc agc ccc agc cgc gac gtg acc aag cac ctg aac gag    433
Lys Val Ile Ala Ser Pro Ser Arg Asp Val Thr Lys His Leu Asn Glu
125                 130                 135                 140 gcc ttc atc gtg atg cag aac cac atg cgc acc ctg gag cac ggc gtg    481
Ala Phe Ile Val Met Gln Asn His Met Arg Thr Leu Glu His Gly Val
                145                 150                 155 gtg ggc gag aac cgc cgc agc gac atc ggc ccc ccc cgc gac gtg ctg    529
Val Gly Glu Asn Arg Arg Ser Asp Ile Gly Pro Pro Arg Asp Val Leu
            160                 165                 170 gtg aag gtg agc gtg aac ggc agc ggc gac ccc cgc atg cga ctg gat    577
Val Lys Val Ser Val Asn Gly Ser Gly Asp Pro Arg Met Arg Leu Asp
        175                 180                 185 acc aac gag agc tac aag ctg gcc ctg cgc ccc agc ggc aac agc ctg    625
Thr Asn Glu Ser Tyr Lys Leu Ala Leu Arg Pro Ser Gly Asn Ser Leu
    190                 195                 200 gtg gtg gac atc acc gcc cac agc ttc tgc ggc gcc cgc cac ggc ctg    673
Val Val Asp Ile Thr Ala His Ser Phe Cys Gly Ala Arg His Gly Leu
205                 210                 215                 220 gag acc ctg ctg cag gtg acc tgg ctg gac ccc tac gcc ggc agc ctg    721
Glu Thr Leu Leu Gln Val Thr Trp Leu Asp Pro Tyr Ala Gly Ser Leu
                225                 230                 235 ctg atc ctg gag gcc gcc acc gtg gtg gac gcc ccc cgc ttc ccc tac    769
Leu Ile Leu Glu Ala Ala Thr Val Val Asp Ala Pro Arg Phe Pro Tyr
            240                 245                 250 cgc ggc ctg ctg ctg gac acc gcc cgc aac ttc ttc ccc gtg agc gag    817
Arg Gly Leu Leu Leu Asp Thr Ala Arg Asn Phe Phe Pro Val Ser Glu
        255                 260                 265 ctg ctg cgg aca atc gac gcc atg gcc gcc aac aag ctg aac acc ttc    865
Leu Leu Arg Thr Ile Asp Ala Met Ala Ala Asn Lys Leu Asn Thr Phe
    270                 275                 280 cac tgg cac gtg agc gac agc cag agc ttc ccc tgg aag ctg gac agc    913
His Trp His Val Ser Asp Ser Gln Ser Phe Pro Trp Lys Leu Asp Ser
285                 290                 295                 300 gcc ccc cag ctg gcc cag cac ggc gcc tac ggc ccc ggc gcc gtg tac    961
Ala Pro Gln Leu Ala Gln His Gly Ala Tyr Gly Pro Gly Ala Val Tyr
                305                 310                 315 acc agc gac gac gtg cgc acc atc gtg aag tac gcc cgc atc cgc ggc    1009
Thr Ser Asp Asp Val Arg Thr Ile Val Lys Tyr Ala Arg Ile Arg Gly
            320                 325                 330 atc cgc gtg ctg atg gag atc gac acc ccc gcc cac gtg ggc cgc gcc    1057
Ile Arg Val Leu Met Glu Ile Asp Thr Pro Ala His Val Gly Arg Ala
        335                 340                 345 ttc ggc tgg ggc ccc gag gcc ggc ctg gga cat ctg gcc cac tgc atc    1105
Phe Gly Trp Gly Pro Glu Ala Gly Leu Gly His Leu Ala His Cys Ile
    350                 355                 360 gag gcc gag ccc tgg agc agc tac tgc ggc gag ccc ccc tgc ggc cag    1153
Glu Ala Glu Pro Trp Ser Ser Tyr Cys Gly Glu Pro Pro Cys Gly Gln
365                 370                 375                 380 ctg aac ccc cgc aac ccc cac atc tac gac ctg ctg gag cac gtg tac    1201
Leu Asn Pro Arg Asn Pro His Ile Tyr Asp Leu Leu Glu His Val Tyr
                385                 390                 395 cgc gag atc atc cag ctg acc ggc gtg gac gac atc ttc cac ctg ggc    1249
Arg Glu Ile Ile Gln Leu Thr Gly Val Asp Asp Ile Phe His Leu Gly
            400                 405                 410 ggc gac gag gtg agc gag cag tgt tgg gct aag cac ttc aac gac acc    1297
Gly Asp Glu Val Ser Glu Gln Cys Trp Ala Lys His Phe Asn Asp Thr
        415                 420                 425
```

-continued

| | | |
|---|---|---|
| gac ccc atg gac ctg tgg atg gag ttc acc cgc cag gcc atg cac gtg<br>Asp Pro Met Asp Leu Trp Met Glu Phe Thr Arg Gln Ala Met His Val<br>430                            435                        440 | 1345 |
| ctg gag cgc gcc aac ggc ggc aag gcc ccc gag ctg acc ctg ctg tgg<br>Leu Glu Arg Ala Asn Gly Gly Lys Ala Pro Glu Leu Thr Leu Leu Trp<br>445                            450                        455                        460 | 1393 |
| agc agc cgc ctg acc cgc agc ccc tac ctg gag cgc ctg gac ccc aag<br>Ser Ser Arg Leu Thr Arg Ser Pro Tyr Leu Glu Arg Leu Asp Pro Lys<br>                      465                        470                        475 | 1441 |
| cgc ttc ggc gtg cac gtg tgg ggc gcc agc cag tgg ccc gag agc cga<br>Arg Phe Gly Val His Val Trp Gly Ala Ser Gln Trp Pro Glu Ser Arg<br>                          480                        485                        490 | 1489 |
| gcc gtc ctg gac gcc ggc ttc cgc agc gtg atc agc cac gtg gac gcc<br>Ala Val Leu Asp Ala Gly Phe Arg Ser Val Ile Ser His Val Asp Ala<br>495                            500                        505 | 1537 |
| tgg tac ctg gac tgc ggc ttc ggc agc tgg cgc gac agc agc gac ggc<br>Trp Tyr Leu Asp Cys Gly Phe Gly Ser Trp Arg Asp Ser Ser Asp Gly<br>510                            515                        520 | 1585 |
| cac tgc ggc ccc tac cgc agc tgg cag cag gtg tac gag cac cgc ccc<br>His Cys Gly Pro Tyr Arg Ser Trp Gln Gln Val Tyr Glu His Arg Pro<br>525                            530                        535                        540 | 1633 |
| tgg gcc acc gag acc ccc gag agt gcc gca tgg ccc gtg gag ggc ggc<br>Trp Ala Thr Glu Thr Pro Glu Ser Ala Ala Trp Pro Val Glu Gly Gly<br>                      545                        550                        555 | 1681 |
| gcc gcc tgc cag tgg acc gag cag ctg ggc ccc ggc ggc ctg gac gcc<br>Ala Ala Cys Gln Trp Thr Glu Gln Leu Gly Pro Gly Gly Leu Asp Ala<br>                      560                        565                        570 | 1729 |
| cgc gtc tgg cct cgc acc gcc gcc ctg gcc gag cgc ctg tgg gcc gac<br>Arg Val Trp Pro Arg Thr Ala Ala Leu Ala Glu Arg Leu Trp Ala Asp<br>                 575                        580                        585 | 1777 |
| cgc gcc gag ggc gcc acc gcc gac gtg tac ctg cgc ctg gac acc cag<br>Arg Ala Glu Gly Ala Thr Ala Asp Val Tyr Leu Arg Leu Asp Thr Gln<br>                      590                        595                        600 | 1825 |
| cgc gcc cgc ctg gtg gcc cgc ggc gtg cgc gcc gcc ccc ctg tgg ccc<br>Arg Ala Arg Leu Val Ala Arg Gly Val Arg Ala Ala Pro Leu Trp Pro<br>605                            610                        615                        620 | 1873 |
| cgc tgg tgc agc cac aac ccc cac gcc tgc ctg tag gcggccgc<br>Arg Trp Cys Ser His Asn Pro His Ala Cys Leu<br>                      625                        630 | 1917 |

<210> SEQ ID NO 12
<211> LENGTH: 631
<212> TYPE: PRT
<213> ORGANISM: Artificial Sequence
<220> FEATURE:
<223> OTHER INFORMATION: Synthetic Construct

<400> SEQUENCE: 12

Met Met Ser Trp Gly Asp Ala Leu Trp Leu Gly Leu Thr Ala Arg Phe
1                  5                      10                      15

Ala Arg Val Gly Arg Leu Arg Arg Ala Val Leu Met Leu Ala Ala Ala
                  20                      25                      30

Ala Cys Thr Ala Ala Ala Val Leu Tyr Trp Lys Gln Gln Thr Asp Asp
                35                      40                      45

Ser Ala Asn Arg Pro Leu His Ser Met Tyr Ser Gly Ile Glu Pro Gln
        50                      55                      60

Trp Ser Trp Leu Cys Gln His Asp Arg Cys Glu Arg Tyr Gln Ala Ser
65                  70                      75                      80

Asp Thr Thr Thr Leu Gln Ser Leu Gln Thr Cys Asn Met Leu Cys Ala
                85                      90                      95

-continued

Ser Thr Gln Leu Trp Pro Gln Pro Thr Gly Pro Val Ser Leu Ala Ser
            100                 105                 110

Ala Ala Val Pro Val Arg Ser Asp Arg Phe Ser Leu Lys Val Ile Ala
        115                 120                 125

Ser Pro Ser Arg Asp Val Thr Lys His Leu Asn Glu Ala Phe Ile Val
    130                 135                 140

Met Gln Asn His Met Arg Thr Leu Glu His Gly Val Val Gly Glu Asn
145                 150                 155                 160

Arg Arg Ser Asp Ile Gly Pro Pro Arg Asp Val Leu Val Lys Val Ser
                165                 170                 175

Val Asn Gly Ser Gly Asp Pro Arg Met Arg Leu Asp Thr Asn Glu Ser
            180                 185                 190

Tyr Lys Leu Ala Leu Arg Pro Ser Gly Asn Ser Leu Val Val Asp Ile
        195                 200                 205

Thr Ala His Ser Phe Cys Gly Ala Arg His Gly Leu Glu Thr Leu Leu
    210                 215                 220

Gln Val Thr Trp Leu Asp Pro Tyr Ala Gly Ser Leu Leu Ile Leu Glu
225                 230                 235                 240

Ala Ala Thr Val Val Asp Ala Pro Arg Phe Pro Tyr Arg Gly Leu Leu
                245                 250                 255

Leu Asp Thr Ala Arg Asn Phe Phe Pro Val Ser Glu Leu Leu Arg Thr
            260                 265                 270

Ile Asp Ala Met Ala Ala Asn Lys Leu Asn Thr Phe His Trp His Val
        275                 280                 285

Ser Asp Ser Gln Ser Phe Pro Trp Lys Leu Asp Ser Ala Pro Gln Leu
    290                 295                 300

Ala Gln His Gly Ala Tyr Gly Pro Gly Ala Val Tyr Thr Ser Asp Asp
305                 310                 315                 320

Val Arg Thr Ile Val Lys Tyr Ala Arg Ile Arg Gly Ile Arg Val Leu
                325                 330                 335

Met Glu Ile Asp Thr Pro Ala His Val Gly Arg Ala Phe Gly Trp Gly
            340                 345                 350

Pro Glu Ala Gly Leu Gly His Leu Ala His Cys Ile Glu Ala Glu Pro
        355                 360                 365

Trp Ser Ser Tyr Cys Gly Glu Pro Pro Cys Gly Gln Leu Asn Pro Arg
    370                 375                 380

Asn Pro His Ile Tyr Asp Leu Leu Glu His Val Tyr Arg Glu Ile Ile
385                 390                 395                 400

Gln Leu Thr Gly Val Asp Asp Ile Phe His Leu Gly Gly Asp Glu Val
                405                 410                 415

Ser Glu Gln Cys Trp Ala Lys His Phe Asn Asp Thr Asp Pro Met Asp
            420                 425                 430

Leu Trp Met Glu Phe Thr Arg Gln Ala Met His Val Leu Glu Arg Ala
        435                 440                 445

Asn Gly Gly Lys Ala Pro Glu Leu Thr Leu Leu Trp Ser Ser Arg Leu
    450                 455                 460

Thr Arg Ser Pro Tyr Leu Glu Arg Leu Asp Pro Lys Arg Phe Gly Val
465                 470                 475                 480

His Val Trp Gly Ala Ser Gln Trp Pro Glu Ser Arg Ala Val Leu Asp
                485                 490                 495

Ala Gly Phe Arg Ser Val Ile Ser His Val Asp Ala Trp Tyr Leu Asp
            500                 505                 510

```
Cys Gly Phe Gly Ser Trp Arg Asp Ser Ser Asp Gly His Cys Gly Pro
        515                 520                 525

Tyr Arg Ser Trp Gln Gln Val Tyr Glu His Arg Pro Trp Ala Thr Glu
    530                 535                 540

Thr Pro Glu Ser Ala Ala Trp Pro Val Glu Gly Gly Ala Ala Cys Gln
545                 550                 555                 560

Trp Thr Glu Gln Leu Gly Pro Gly Gly Leu Asp Ala Arg Val Trp Pro
                565                 570                 575

Arg Thr Ala Ala Leu Ala Glu Arg Leu Trp Ala Asp Arg Ala Glu Gly
            580                 585                 590

Ala Thr Ala Asp Val Tyr Leu Arg Leu Asp Thr Gln Arg Ala Arg Leu
        595                 600                 605

Val Ala Arg Gly Val Arg Ala Ala Pro Leu Trp Pro Arg Trp Cys Ser
    610                 615                 620

His Asn Pro His Ala Cys Leu
625                 630
```

METHOD FOR PRODUCING GLYCOPROTEIN HAVING MANNOSE RESIDUE AS NON-REDUCING END OF SUGAR CHAIN

The instant application contains a Sequence Listing which has been submitted electronically in ASCII format and is hereby incorporated by reference in its entirety. Said ASCII copy, created on Oct. 5, 2011, is named GP149-PCT ST25 and is 31,725 bytes in size.

TECHNICAL FIELD

The present invention relates to a method of producing glycoproteins which have mannose residues at non-reducing ends of their sugar chains, using mammalian cells.

BACKGROUND ART

In mammalian cells, N-glycosidic bond-linked sugar chains of glycoproteins are those attached to asparagine residues of the proteins, through a complex pathway involving various enzymes, while the proteins, after translated from RNA, are transferred through the lumen of an endoplasmic reticulum to Golgi bodies. The major types of N-glycosidic bond-linked sugar chains are complex-type sugar chains and high mannose-type sugar chains. High mannose-type sugar chains are mainly of the structure represented by structural formula 1 below. Complex-type sugar chains, while there are various types of them, are characterized in that their non-reducing ends consist of sialic acid residues. An example of them is shown in structural formula 2 below. The region shown by structural formula 3 below, which is common to both complex-type and high mannose-type sugar chains, is called the core region.

[Chem. 1]

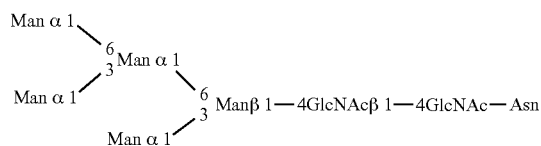

Structural formula 1

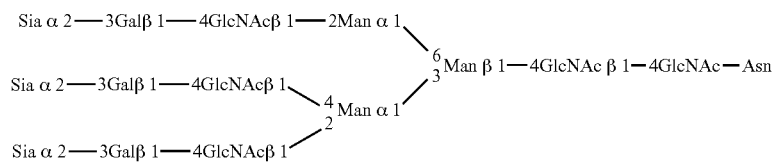

Structural formula 2

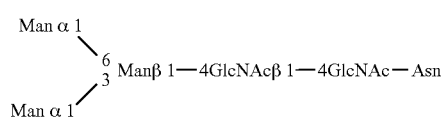

Structural formula 3

High mannose-type and complex-type sugar chains are biosynthesized as follows. First, dolichol-P-P-GlcNAc$_2$Man$_9$Glc$_3$, an intermediate which includes two N-acetylglucosamine (GlcNAc), nine mannose (Man), and three glucose (Glc) residues, is transferred, by an oligosaccharyltransferase complex, to an asparagine residue of a protein being synthesized by translation in the lumen of an endoplasmic reticulum, and attached as a sugar chain represented by structural formula 4 below.

[Chem. 2]

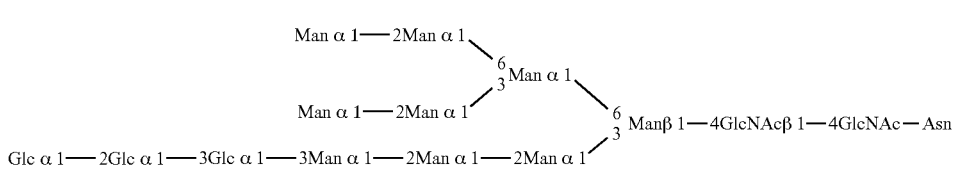

Structural formula 4

In the lumen of endoplasmic reticulum, then, from the non-reducing end of the sugar chain of structural formula 4 are removed three Glc's by glucosidase and then one Man by ER mannosidase, which leaves the sugar chain having a structure represented by structural formula 5 below.

[Chem. 3]

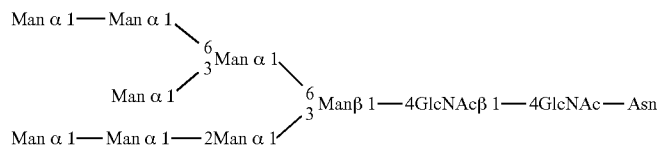

This glycoprotein then is transferred to Golgi bodies, where Golgi mannosidase I removes three Man's from the sugar chain of structural formula 5, leaving the high mannose-type sugar chain of structural formula 1 shown above, in which two Man's bind to the core region.

Complex-type sugar chains are formed in Golgi bodies by additional modifications on the high mannose-type sugar chain. Namely, the route through which the complex-type sugar chain of structural formula 2 is formed is as follows. First, one GlcNAc is bound to the high mannose-type sugar chain (structural formula 1) by N-acetylglucosamine transferase I, forming a sugar chain of the structure shown by structure formula 6 below. Two Man's then are removed by Golgi mannosidase II, which leaves the sugar chain structure shown by structural formula 7 below, in which one GlcNAc binds to the core region.

[Chem. 4]

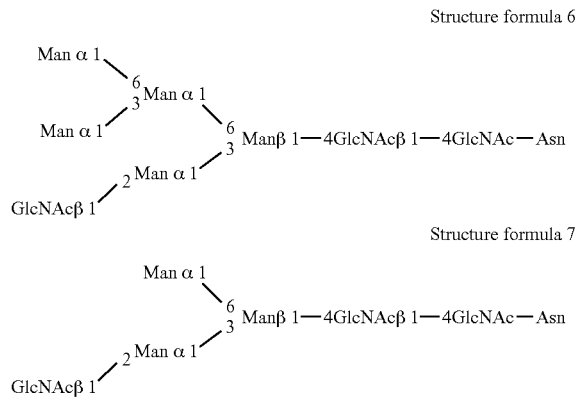

Then, two GlcNAc, three galactose (Gal), and three sialic acid (Sia) residues are bound to it to form the complex-type sugar chain of structural formula 2. Other complex-type sugar chains also exist in which a fucose residue is bound to the GlcNAc molecules that binds directly to the asparagine residue.

If mammalian cells, such as Chinese hamster ovary cells (CHO cells), are used in producing a recombinant glycoprotein, many of the sugar chains of the protein thus obtained will be a complex-type in their structure, and sialic acid residues thus will occur at the non-reducing ends of the sugar chains of such a recombinant glycoprotein. It is known that stability in the blood of a recombinant protein administered to a body is increased if complex-type sugar chains, which have a sialic acid residues at their non-reducing ends, are attached to the protein (cf. Patent Document 1). Thus, when recombinant glycoproteins are produced which exhibit their effects while circulating in the blood, production methods using CHO cells are utilized, with which sugar chains are produced having sialic acid residues at their non-reducing ends, expecting elongation of their half-lives in the blood, and thereby augmentation of their pharmacological effects. Erythropoietin and follicle-stimulating hormone (FSH) are typical examples of such recombinant glycoproteins (cf. Patent Documents 2 and 3).

Some of recombinant glycoproteins, however, having sugar chains of a complex-type would be rather disadvantageous. Among them, for example, are a group of enzymes, such as glucocerebrosidase, which are administered to patients in enzyme replacement therapy for lysosomal storage diseases. To be effective, such enzymes must be taken up into cells following their administration to a body. Their cellular uptake is made via mannose receptors expressed on the cell membrane of target cells (cf. Non-patent Document 1). And, for glycoproteins to be taken up via the mannose receptors, the structure of sugar chains of the glycoproteins must be that of the high mannose-type sugar chain, whose non-reducing ends consist of mannose residues. Therefore, in such enzyme replacement therapy, enzymes whose sugar chains are of a complex-type cannot be employed.

Besides, as for a drug which is required to have a short half-life in blood, it is not desirable that the drug should have non-reducing ends which are those of complex-type sugar chains, because they would increase its stability in blood. In such a case, too, the sugar chains are required to be of a high mannose-type.

Thus, attempts have been made to establish a method for producing glycoproteins having high mannose-type sugar chains. For example, there is a method in which glycoproteins are once produced with complex-type sugar chains using mammalian cells, and then treated with three enzymes, sialidase, β-galactosidase, and hexosaminidase, to remove sialic acid, galactose, and N-acetylgalactosamine residues from the non-reducing ends, thereby leaving mannose residues behind at the non-reducing ends. A glucocerebrosidase pharmaceutical preparation for treatment of Gaucher's disease currently marketed by Genzyme Corp. (product name: CEREZYME® Injection 200; cf. Non-patent Document 2) is produced by this method. However, as it requires the additional processes of enzyme treatment, this method involves problems of complexity and increased costs.

There is also known a method, in which mammalian cells are cultured in the presence of kifunesine when inducing the cells to express a glycoprotein (cf. Patent document 4). As kifunesine is an inhibitor of ER mannosidase, it terminates the modification process of sugar chains following removal of a glucose residue by glucosidase, just before the step by ER mannosidase, providing as a result a glycoprotein having a sugar chain with the structure shown by structural formula 8 below, which has three mannose residues at its non-reducing ends. This method, however, has drawbacks, such as safety concern of the final product, for an enzyme inhibitor must be added in the process of its synthesis.

[Chem. 8]

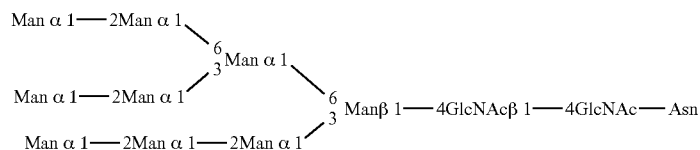

Structural formula 8

Further, there is known still another method, in which LEC-1 cells, CHO mutant cells lacking N-acetylglucosamine transferase I activity, are used (cf. Non-patent Document 3). N-acetylglucosamine transferase is an enzyme which catalyzes the early reaction in the pathway through which complex-type sugar chains are synthesized starting with the high mannose-type sugar chain, and binds one GlcNAc residue to the high mannose-type sugar chain (structural formula 1) to give rise to the sugar chain of the structure shown by structural formula 6 above. Because of the lack of this enzyme, LEC-1 cells do not produce complex-type sugar chains from the high mannose-type sugar chain, thus giving glycoproteins having the structure of the high mannose-type sugar chain. However, the method of production of glycoproteins utilizing LEC-1 cells is not productive enough (Non-patent Document 4).

An expression system using insect cells is known for a method of producing glycoproteins having mannose residues at their non-reducing ends (cf. Patent Document 5). It is known that insect cells produce glycoproteins having N-glycosidic bond-linked sugar chains shown by the structural formula 3 above (paucimannose-type sugar chains), formed of two GlcNAc's and three Man's (cf. Non-patent Document 5). That is, in insect cells, a pathway is dominant in which GlcNAc at the non-reducing end in structural formula 7 is removed by β-N-acetylglucosaminidase to leave the paucimannose-type sugar chain behind, thus giving glycoproteins having mannose residues at the non-reducing end (cf. Non-patent Document 6).

An expression system using cabbage armyworm (*Spodoptera frugiperda*)-derived cells (Sf-9, etc.) is one of common expression systems utilizing insect cells (Patent Document 6). It is known that *Spodoptera frugiperda* has three types of β-N-acetylglucosaminidases; β-N-acetylglucosaminidase 1, β-N-acetylglucosaminidase 3 (cf. Non-patent Documents 7 and 8), and SfFDL (cf. Patent Document 7), which are enzymes with activity to remove GlcNAc from non-reducing ends of sugar chains. Another enzyme having similar activity, e.g., BmFDL, is also isolated from silk worm (*Bombyx mori*) (Non-patent Document 9). However, as there are definite species differences between insect cells and mammalian cells (in particular human cells), employment of insect cells in production of medical drugs is thought to be undesirable because of concerns about various influences which the product would have received in the process of its biosynthesis in insect cells.

In addition, an expression system using plant-derived cells is known as a method using cells other than mammalian cells for for production of glycoproteins having mannose residues at the non-reducing ends, (Patent Document 8).

PRIOR ART DOCUMENTS

Patent Documents

[Patent Document 1] JP Patent Application Publication No. H08-027181
[Patent Document 2] JP Patent Application Publication No. 2004-525342
[Patent Document 3] WO 2009/127826
[Patent Document 4] JP Patent Application Publication No. 2004-506438
[Patent Document 5] JP Patent Application Publication No. 2009-225781
[Patent Document 6] JP Patent Application Publication No. H02-291270
[Patent Document 7] WO 2009/079376
[Patent Document 8] JP Patent Application Publication No. 2006-524506

Non-Patent Documents

[Non-patent Document 1] Sato Y. et al., J Clin Invest. (1993) 91, 1909-17
[Non-patent Document 2] Cerezyme Injection 200, Package Insert
[Non-patent Document 3] Ripka J. et al., J Cell Biochem. (1990) 42, 117-22
[Non-patent Document 4] Van Patten S M. et al., Glycobiology (2007) 17, 467-78
[Non-patent Document 5] Watanabe S. et al., J Biol Chem. (2002) 277, 5090-3
[Non-patent Document 6] Altmann F. et al., J Biol Chem. (1995) 270, 17344-9
[Non-patent Document 7] Tomiya N. et al., J Biol Chem. (2006) 281, 19545-60
[Non-patent Document 8] Aumiller J J. et al., Prot. Expr. Purif. (2006) 47, 571-90
[Non-patent Document 9] Nomura T. Et al., J Biosci Bioeng. (2010) 110, 386-91

SUMMARY OF INVENTION

Technical Problem

Against the above-background, the objective of the present invention is to provide a novel method for production of recombinant glycoproteins having mannose residues at the non-reducing ends of their N-glycosidic bond-linked sugar chains, using mammalian cells, esp. CHO cells.

In the study directed to the above objective, the present inventors attempted to introduce into mammalian cells a system of insect cells in which the high mannose-type sugar chains are dominantly synthesized. As a result, the inventors surprisingly found that recombinant glycoproteins are obtained that have mannose residues at the non-reducing ends of their N-glycosidic bond-linked sugar chains, by using transformant mammalian cells which were prepared by introducing a β-N-acetylglucosaminidase gene into mammalian cells to let the gene express itself.

Thus, the present invention provides what follows.

(1) A transformant mammalian cell having an exogenous β-N-acetylglucosaminidase gene introduced and allowed to express itself therein.

(2) The transformant mammalian cell according to (1) above, wherein β-N-acetylglucosaminidase expressed following introduction of the β-N-acetylglucosaminidase gene exhibits the activity thereof in Golgi bodies.

(3) The transformant mammalian cell according to (1) or (2) above, wherein the β-N-acetylglucosaminidase gene is of insect origin.

(4) The transformant mammalian cell according to (3) above, wherein the insect is an insect of Lepidoptera.

(5) The transformant mammalian cell according to (4) above, wherein the insect of Lepidoptera is *Spodoptera frugiperda* or *Bombyx mori*.

(6) The transformant mammalian cell according to (5) above, wherein the β-N-acetylglucosaminidase gene is one or more genes selected from the group consisting of β-N-acetylglucosaminidase 1 gene, β-N-acetylglucosaminidase 3 gene, SfFDL gene, and BmFDL gene.

(7) The transformant mammalian cell according to one of (1) to (6) above having an exogenous gene encoding a predetermined glycoprotein further introduced and allowed to express itself so as to produced the predetermined glycoprotein.

(8) The transformant mammalian cell according to (7) above, wherein the exogenous gene encoding the predetermined glycoprotein is a gene of human origin.

(9) The transformant mammalian cell according to (8) above, wherein the gene of human origin is a gene encoding a lysosomal enzyme.

(10) The transformant mammalian cell according to (9) above, wherein the lysosomal enzyme is selected from the group consisting of glucocerebrosidase, acid sphingomyelinase, lysosomal acid lipase, acid α-glucosidase, N-acetylgalactosamine-4-sulfatase, iduronate-2-sulfatase, α-L-iduronidase, α-galactosidase A, hexosaminidase, α-N-acetylgalactosaminidase, α-mannosidase, and sialidase.

(11) The transformant mammalian cell according to (9) above, wherein the lysosomal enzyme is glucocerebrosidase.

(12) A method for production of a glycoprotein having N-glycosidic bond-linked sugar chains, wherein all or part of the non-reducing ends of the sugar chains comprise mannose residues, wherein the method comprises the steps of:

(a) culturing the mammalian cell according to one of (1) to (6) above in a medium to allow the glycoprotein be expressed, and (b) purifying the glycoprotein expressed in (a) above.

(13) The method for production according to (12) above, wherein the mammalian cell according to (7) above is employed instead of the cell according to one of (1) to (6) above.

(14) The method for production according to (13) above, wherein the exogenous gene encoding the glycoprotein is a gene of human origin.

(15) The method for production according to (14) above, wherein the gene of human origin is a gene encoding a lysosomal enzyme.

(16) The method for production according to (15) above, wherein the lysosomal enzyme is selected from the group consisting of glucocerebrosidase, acid sphingomyelinase, lysosomal acid lipase, acid α-glucosidase, N-acetylgalactosamine-4-sulfatase, iduronate-2-sulfatase, α-L-iduronidase, α-galactosidase A, hexosaminidase, α-N-acetylgalactosaminidase, α-mannosidase, and sialidase.

(17) The method for production according to (15) above, wherein the lysosomal enzyme is glucocerebrosidase.

Effect of Invention

Mammalian cells transformed with an insect β-N-acetylglucosaminidase gene according to the present invention are modified in their characteristics in such a manner that mannose residues occur at an increased proportion in the non-reducing ends of the N-glycosidic bond-linked sugar chains of glycoproteins produced by the cells. Therefore, the cells produces their original, intrinsic glycoproteins in a modified form in which at least part of, or all of, the non-reducing ends of their N-glycosidic bond-linked sugar chains are mannose residues. Further, the transformant mammalian cells, if employed, instead of natural mammalian cells, for expression of an introduced exogenous glycoprotein gene, allows production of the glycoprotein in such a form which were unavailable using natural mammalian cells, namely, in the form that the non-reducing ends of its sugar chains consist partly, or more frequently, of mannose residues, or preferably entirely of mannose residues.

Thus, the present invention enables production of glycoproteins with an increased proportion of mannose residues occurring at the non-reducing ends of their N-glycosidic bond-linked sugar chains, without employing insect cells. Glycoproteins so far produced using mammalian cells had complex-type sugar chains as their N-glycosidic bond-linked sugar chains and therefore had to be further treated with enzymes so that mannose residues come to occur at the non-reducing ends of the sugar chains. In contrast, the present invention enables direct production of glycoproteins in which all or part of the non-reducing ends of their N-glycosidic bond-linked sugar chains consist of mannose residues. According to the method of the present invention, therefore, glycoproteins having mannose residues as the non-reducing ends of their N-glycosidic bond-linked sugar chains can be obtained more efficiently and more easily than before. Further, glycoproteins obtained according to the present invention are useful as such medicaments that must be taken up by target cells via mannose receptors on the cells or which must have a short half life in blood.

BRIEF DESCRIPTION OF DRAWINGS

FIG. 1-2 A flow diagram of the method for constructing pE-neo vector is shown.

FIG. 2-1 A flow diagram of the method for constructing pE-hygr vector is shown.

FIG. 2-2 A flow diagram of the method for constructing pE-hygr Vector is shown.

FIG. 2-3 A flow diagram of the method for constructing pE-hygr Vector is shown.

FIG. 3 A figure showing the patterns of electrophoretic migration of glucocerebrosidase (GBA). (Lane 1: culture supernatant of GBA expressing cells, Lanes 2-4: culture supernatant of GBA expressing cells sequentially treated with sialidase, β1, 4-galactosidase, and β-N-acetylglucosaminidase, Lane 5: culture supernatant of GBA/AcGlcNAcase-3 expressing cells)

MODE FOR CARRYING OUT THE INVENTION

Figure 1:
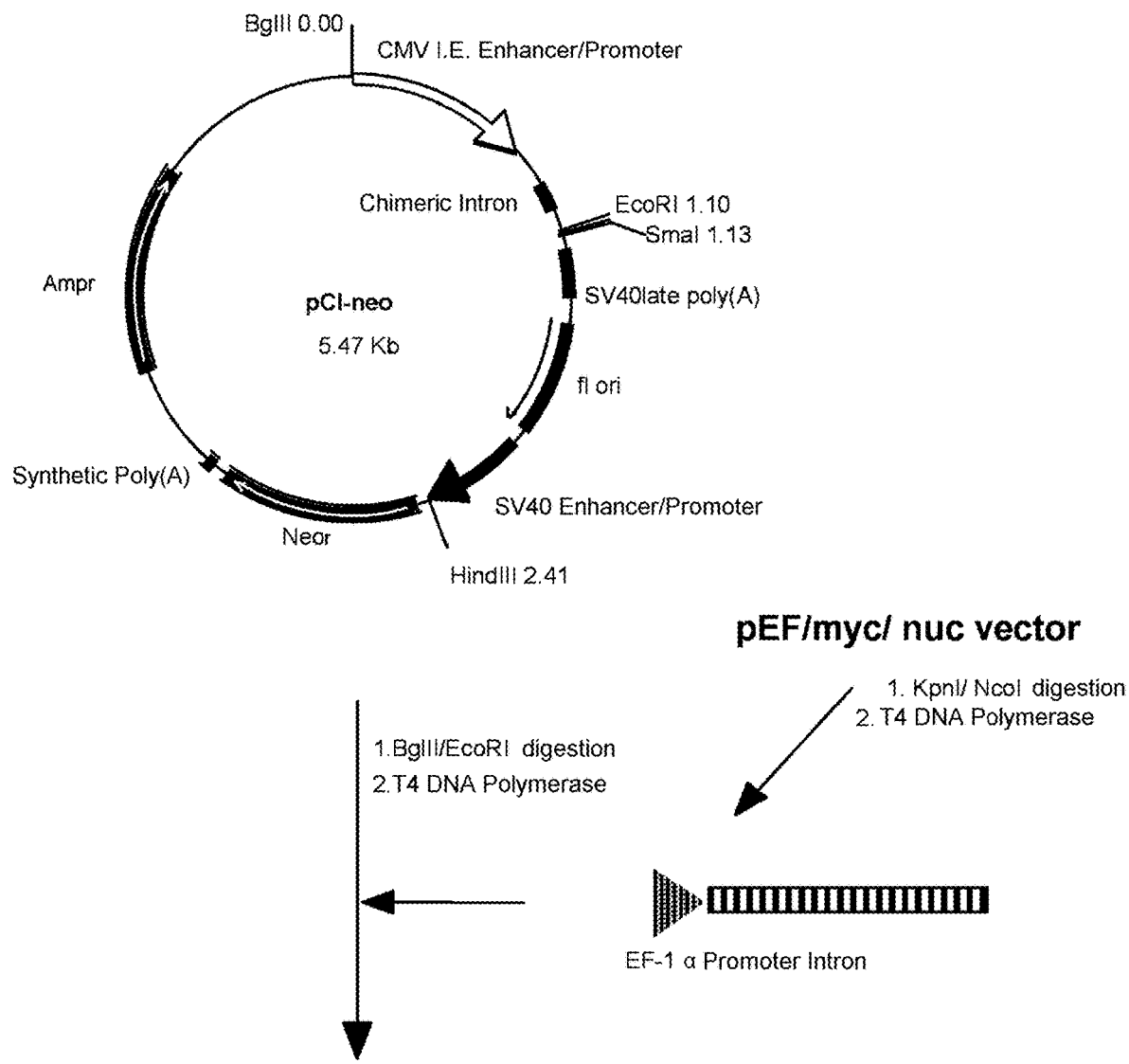
FIG. 1-1 A flow diagram of the method for constructing pE-neo vector is shown.

In the present invention, the term "mammalian animal" includes, without particular limitation, any mammalian animals, but preferably represents primates such as human, African green monkey, and the like; rodents such as mouse, rat, Chinese hamster, and the like; rabbit, and canine. The term "mammalian cells" includes, without particular limitation, any cells derived from a mammalian animal, either primary or subcultured cells, collected from an organ taken out of the body, or from muscle tissue, skin, connective tissue, nerve tissue, blood, bone marrow, and the like, or their cell lines established so as to keep their characteristics through repeated subcultures. Further, those cells may be either normal cells or cells which have become cancerous. Cells which can be used particularly preferably are CHO cells, derived from the ovary of a Chinese hamster, human fibroblasts, and COS cells, derived from the renal fibroblast of an African green monkey.

In the present invention, the term "β-N-acetylglucosaminidase" means an enzyme that has an activity of releasing β-glycosidic-bond-linked N-acetylglucosamine residues occurring at the non-reducing ends of sugar chains (e.g., the N-acetylglucosamine occurring at the non-reducing end in the structural formula 6 or 7). There is no particular limitation as to the gene itself that encodes β-N-acetylglucosaminidase insofar as the β-N-acetylglucosaminidase encoded by the gene has the activity defined above. For example, any of such genes may be employed, either wild-type genes originating directly from organisms, or mutant-type genes obtained through introduction of mutation such as substitution, insertion, or deletion of one or more nucleotides of those wild-type genes, or artificially designed genes. Further, there is no particular limitation as to species of the organisms, and such genes originating from any organisms including mammal may be employed, among which preferred are, for example, insects of Lepidoptera, such as silk worm (*Bombyx mori*), cabbage armyworm (*Spodoptera frugiperda*), and measuring worm (Geometridae); those of Diptera, such as drosophila (*Drosophila*); prokaryotes, such as *bacillus*; nematodes; yeasts; actinomycetes; ascomycetes; basidiomycete; and plants. Among these, preferred are genes originating from insects, in particular those of Lepidoptera, and most particularly silk worm and cabbage armyworm.

Examples of useful β-N-acetylglucosaminidase genes originating from organisms include, e.g., β-N-acetylglucosaminidase 1 and β-N-acetylglucosaminidase 3 genes, and SfFDL gene originating from cabbage armyworm; BmFDL gene originating from silk worm. A β-N-acetylglucosaminidase gene constructed by fusion of fragments of β-N-acetylglucosaminidase genes from two or more organisms could also be used.

In the present invention, β-N-acetylglucosaminidase to be expressed in mammalian cells acts as an enzyme which releases N-acetylglucosamine residues occurring at the non-reducing end in, for example, the above structural formula 6 and structural formula 7, in the synthetic pathway of N-glycosidic bond-linked sugar chains in the cells. Therefore, it is desirable that the enzyme exhibits its activity in the Golgi bodies, the organelle where the N-glycosidic bond-linked sugar chains are synthesized in mammalian cells.

It is known that proteins which are localized in these organelles in mammalian cells generally have a localization signal within their amino acid sequences. Therefore, a β-N-acetylglucosaminidase gene introduced according to the present invention may be a chimeric β-N-acetylglucosaminidase gene constructed by fusing a gene fragment encoding the enzymatic active site of β-N-acetylglucosaminidase with a gene fragment encoding the localization signal of some other protein, in order to localize it to the organelles more efficiently.

In the present invention, as transformation of mammalian cells with β-N-acetylglucosaminidase gene is performed for the purpose of making the mammalian cells express the β-N-acetylglucosaminidase, any method may be employed for the transformation as long as it meets this purpose. In general, the transformation may be carried out by introducing an expression vector with an incorporated β-N-acetylglucosaminidase gene into mammalian cells. There is no particular limitation as to such a expression vector to be employed so long as it can express a β-N-acetylglucosaminidase gene in the mammalian cells to which it is introduced. Generally, an expression vector is an circular plasmid, which is introduced into cells either without alteration of its circular configuration or after cut open with a restriction enzyme. A β-N-acetylglucosaminidase gene is incorporated into an expression vector which can regulates expression of the gene, downstream of its promoter, so that the gene is expressed in the mammalian cells. Promoters which may be utilized may be those derived from cytomegalovirus (CMV), SV40 early promoter, elongation factor 1 (EF-1) promoter, and the like.

Alternatively, the above transformation may be performed, for example, through fusion of a mammalian cell with a cell, e.g., an insect cell which expresses β-N-acetylglucosaminidase. In the present specification, a mammalian cell thus prepared by fusion is also included in a mammalian cell transformed with β-N-acetylglucosaminidase gene. Besides, the mammalian cell may be transformed not only with a single β-N-acetylglucosaminidase gene or but with two or more different β-N-acetylglucosaminidase genes.

In the present invention, transformation of mammalian cells with an exogenous gene encoding a glycoprotein is performed so that the glycoprotein is produced by the mammalian cells, and therefore it may be performed by any method so long as this purpose is met. Such transformation may be performed in a similar manner as the transformation of mammalian cells described above with the β-N-acetylglucosaminidase gene.

In the present invention, while there is no particular limitation as to exogenous genes encoding a glycoproteins to be incorporated into an expression vector, they are preferably genes encoding such glycoproteins as have to be taken up by cells via their mannose receptors after they are administered to a body, and most preferably are genes encoding lysosomal enzymes, such as glucocerebrosidase, acid sphingomyelinase (sphingomyelin phosphodiesterase), and the like. A glucocerebrosidase obtained by the method for production according to the present invention may be used in enzyme replacement therapy of patients with Gaucher's disease, acid sphingomyelinase patients with Niemann-Pick disease, lysosomal acid lipase patients with Wolman disease, acid α-glucosidase (acid maltase) patients with Pompe disease, N-acetylgalactosamine-4-sulfatase patients with Maroteaux-Lamy syndrome, iduronate-2-sulfatase patients with Hunter syndrome, α-L-iduronidase patients with Hurler syndrome, and α-galactosidase A patients with Fabry disease, respectively. Besides, the method for production according to the present invention may be utilized to produce enzymes, such as hexosaminidase, α-N-acetylgalactosaminidase, α-mannosidase, sialidase, and the like.

In addition, production of a glycoprotein using mammalian cells may be performed not by introduction of an exogenous gene, but by inducing an increased expression of the intrinsic gene encoding a glycoproteins of interest in mammalian cells having a capacity of producing the glycoprotein. The term "intrinsic gene" referred to herein means a gene which is originally on the genome of the mammalian cells employed. There is no particular limitation as to the method by which to induce an increased expression of an intrinsic gene, and any of well-known methods may be employed as desired. They include, for example, a method in which a cytomegalovirus (CMV)-derived promoter is introduced in the intrinsic gene at its expression regulating site, by homologous recombination (WO 94/12650); a method in which a compound which acts on the expression regulating site of a particular intrinsic gene to increase the amount of its expression, such as a hormone, growth factor, vitamin, cytokine, interleukin, or the like, is added to the culture medium. For example, a steroid hormone, thyroid hormone, retinoic acid, vitamin B, and the like are capable of activating, via their respective receptors, an intrinsic gene which has a hormone-responding sequence at its expression regulating-site to increase the amount of its expression.

As a glycoprotein obtained by the present invention has mannose residues as at least part or all of the residues occurring at the non-reducing ends of the N-glycosidic bond-linked sugar chain, the glycoprotein is not only taken up by cells through their mannose receptors but also exhibits altered stability and dynamics in the blood when administered to the body as compared with a N-glycosidic bond-linked sugar chain which is of a complex-type. Therefore, the present invention may also be utilized to alter the stability in the body, and the dynamics in the blood, of a glycoprotein. Namely, while the sialic acid residues occurring at the non-reducing ends of complex-type sugar chains have an effect of enhancing stability of the glycoproteins in the body, the present invention can be utilized, for example, to obtain a glycoprotein having a shorter half life in the blood when administered to the body. If a medicament with which a side effect is anticipated remains in the body for an elongated period of time, development of the side effect might be promoted. In such a case, a medicament comprising a glycoprotein with the shorter half life can be produced using the present invention.

While the present invention is described in further detail with reference to the examples, it is not intended that the present invention be limited to the examples.

Figures 1, 2:
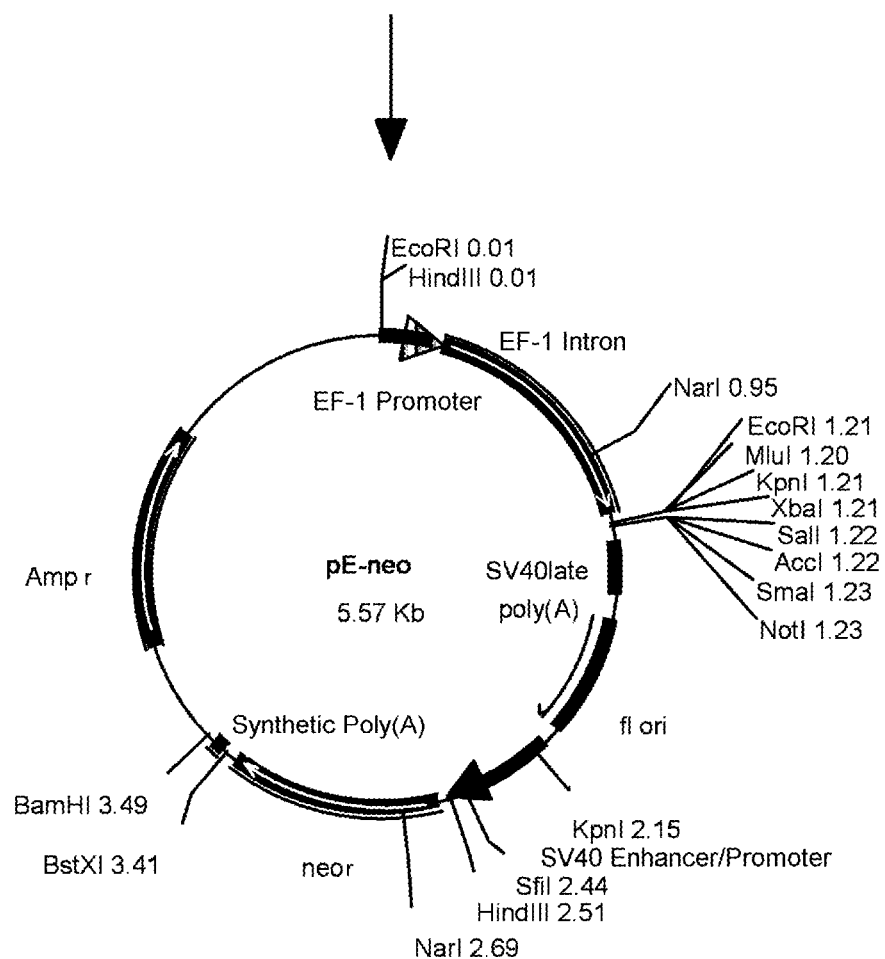

[Construction of pE-Neo Vector and pE-Hygr Vector]

pEF/myc/nuc vector (Invitrogen) was digested with KpnI and NcoI to cut out a region which includes EF-1α promoter and its first intron. This was blunt-ended with T4 DNA polymerase. pCI-neo (Invitrogen), after digested with BglII and EcoRI to remove a region containing CMV enhancer/promoter and introns, was blunt-ended with T4 DNA polymerase. Into this was inserted the region including EF-1α promoter and its first intron mentioned above to construct pE-neo vector (FIG. 1-1 and FIG. 1-2).

pE-neo vector was digested with SfiI and BstXI to cut off a region of about 1 kbp containing neomycin-resistant gene (FIG. 2-1). Hygromycin gene was amplified by PCR using pcDNA3.1/Hygro(+) (Invitrogen) as a template and primer Hyg-Sfi (5'-GAGGCCGCCTCGGCCTCTGA-3'; SEQ ID NO:1) and primer Hyg-BstX (5'-AACCATCGTGATGGGTGCTATTCCTTTGC-3'; SEQ ID NO:2) (FIG. 2-2). Hygromycin genes thus amplified then was digested with SfiI and BstXI and inserted into pE-neo vector mentioned above to construct pE-hygr vector (FIG. 2-3).

[Construction of Glucocerebrosidase-Expressing Cells]

Glucocerebrosidase gene (GBA gene) was amplified by PCR using human placenta cDNA library A (TAKARA) as a template and primer GBA-Mlu (5'-GCAATACGCGTCCGCCACCATGGAGTTTT-CAAGTCCTTCCAGAGAGG-3'; SEQ ID NO:3) and primer GBA-Not (5'-GGACGCGGCCGCGAGCTCT-CACTGGCGACGCCACAGGTAGG-3'; SEQ ID NO:4). The gene thus amplified was digested with restriction enzymes (MluI and NotI), inserted into pCI-neo (Promega) between its MluI and NotI sites, and the vector thus obtained was designated pCI-neo(GBA). After having checked that no mutation occurred in the nucleotide sequence of GBA gene introduced into pCI-neo on a DNA sequencer (ABI), pCI-neo(GBA) was digested with restriction enzymes (MluI and NotI) to cut out GBA gene. The GBA gene thus cut out was inserted into the above-constructed expression vector, pE-neo, between its MluI and NotI sites, and the vector thus obtained was designated GBA expression vector [pE-neo (GBA)]. CHO-K1 cells, after transformed with pE-neo (GBA) using lipofectamin 2000 reagent (Invitrogen), were subjected to selective culture in CD Opti CHO medium (Invitrogen) containing G418 to select glucocerebrosidase-expressing cells (GBA-expressing cells).

[Construction of β-N-Acetylglucosaminidase 3 Expression Plasmid]

Using QUICKPREP Total RNA Extraction Kit (Amersham Pharmacia), total RNA was extracted from Sf9 cells (Invitrogen), which originated from *Spodoptera frugiperda*, and a reverse transcription reaction was performed using an oligo dT, as a primer, and SUPERSCRIPT Choice System for cDNA Synthesis (GIBCO BRL). Using the reverse transcript obtained as a template, PCR was performed using primer sets: primer N-AGase5'-Sal (5'-CCGGTCGAC-CATGTTACGGCACGTAATATTGTTATTCG-3'; SEQ ID NO:5) and primer N-AGase5'-Mlu (5'-ACCAATCAGTT-TATAGGTGAT-3'; SEQ ID NO:6); and primer N-AGase3'-Mlu (5'-GAAGTACACCCACAGAGGTC-3'; SEQ ID NO:7) and primer N-AGase3'-Not (5'-GCTTGCGGCCGCCTAAAAGTAATTCCCTGT-TACGCAAAATCC-3'; SEQ ID NO:8), two halves, 5'-side and 3'-side, of β-N-acetylglucosaminidase 3 gene were separately amplified. The 5'-side DNA fragment thus obtained was digested with restriction enzymes (SalI and MluI), and the 3'-side DNA fragment with restriction enzymes (MluI and NotI). The 5'-side DNA fragment thus obtained was inserted into pCI-neo between its SalI and MluI sites, and the 3'-side DNA fragment into pCI-neo between its MluI and NotI sites, and the products thus obtained were designated pCI-neo(N-AGase5') and pCI-neo(N-AGase3'), respectively. After having checked, on a DNA sequencer (ABI), that the fragments of β-N-acetylglucosaminidase 3 gene introduced into pCI-neo were free of mutations in their nucleotide sequences, pCI-neo(N-AGase5') was digested with SalI and MluI, and pCI-neo(N-AGase3') with MluI and NotI, respectively, to cut out the 5'-side DNA fragment and 3'-side DNA fragment. The 5'-side DNA fragment and 3'-side DNA fragment then were incorporated into pBluescript SK(−) (Toyobo) between its SalI and NotI sites so that the full length β-N-acetylglucosaminidase 3 gene was reconstructed. The product thus obtained was designated pBSK(N-AGase). pBSK(N-AGase) was digested with SalI and NotI to cut out β-N-acetylglucosaminidase 3 gene, which then was inserted into the expression vector pE-hygr constructed above between its SalI and NotI sites. The product thus obtained was designated, β-N-acetylglucosaminidase 3 gene expression plasmid [pE-hygr (N-AGase)].

[Introduction of β-N-Acetylglucosaminidase 3 Gene into GBA Expression Cells]

pE-hygr(N-AGase) was introduced into GBA expressing cells by electroporation, and the cells then were subjected selective culture in CD Opti CHO medium containing 200 μM hygromycin and 500 μg/mL G418. This gave GBA expressing cells which were transformed with β-N-acetylglucosaminidase 3 gene.

[Selective Culture with Kidney Bean Lectin (PHA-L4 and PHA-E4)]

Kidney bean lectin has two subunits, L and E-types. L-type subunit recognizes tetraantennary complex-type sugar chains, and E-type subunit bisecting diantennary complex-type sugar chains. PHA-L4 is a isolectin which is a tetramer consisting of L-type subunits alone, and PHA-E4 of E-type subunits alone. When cells are treated with high concentrations of them, these lectins bind to the cells via membrane proteins having complex-type sugar chains that have sialic acid residues at their non-reducing ends, and the cells are killed as a result. Further, lectins cross-link the cells to make them aggregate. On the other hand, if the sugar chains of membrane proteins are modified so as to have mannose residues at their non-reducing ends, lectins can no longer bind to the cells and thus the cells can grow. The above transformant cells, which were obtained by introduction of pE-hygr(N-AGase) into GBA expressing cells by electroporation, followed by selective culture, were cultured in CD Opti CHO medium containing 12 μg/mL PHA-L4 (J Oil Mills) and 12 μg/mL PHA-E4 (J Oil Mills). Thus, among the transformant cells, those which expressed complex-type sugar chains were annihilated and aggregated, which allowed collection of non-aggregated cells. The non-aggregated cells collected were designated GBA/AcGlcNAcase-3 expressing cells.

[Analysis of Structure of Sugar Chain by Western Blotting]

Figures 1, 2:
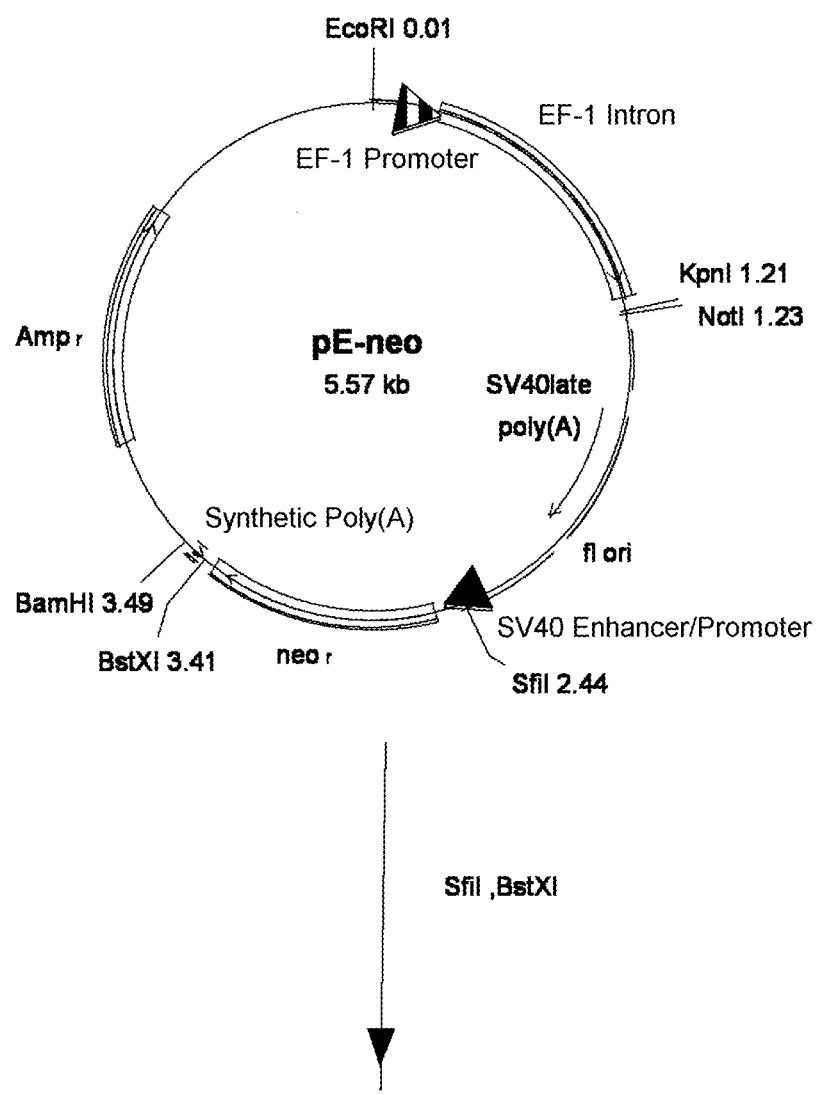
Figure 2:
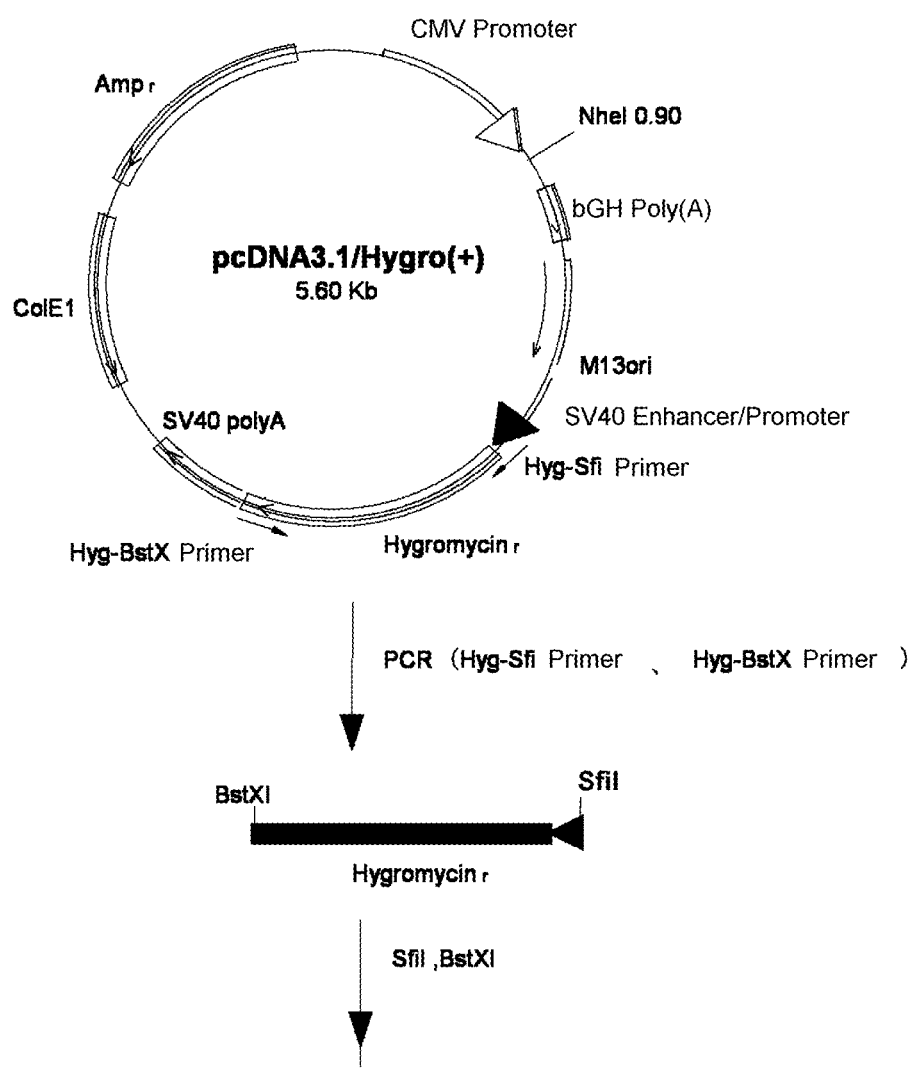
Figures 2, 3:
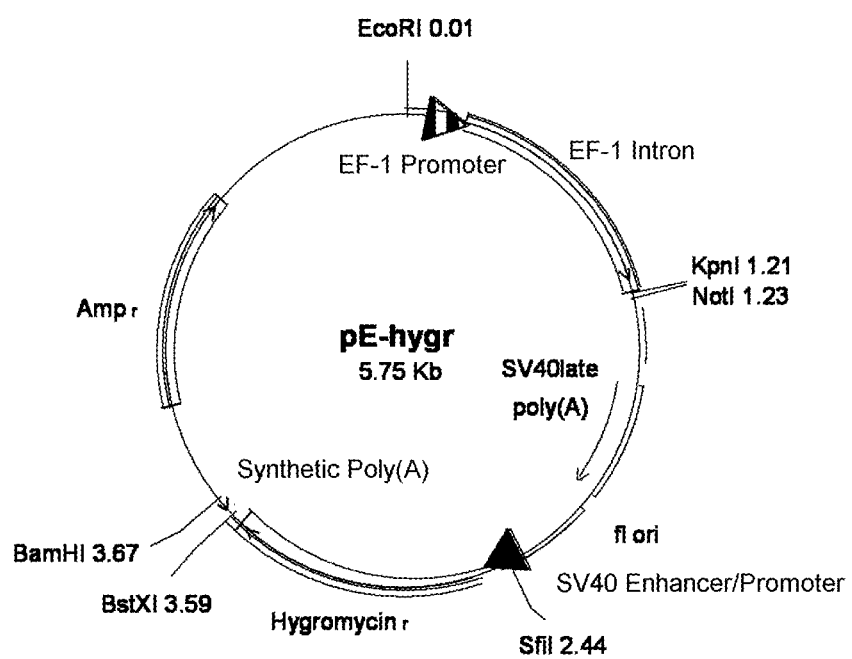
Figure 3:
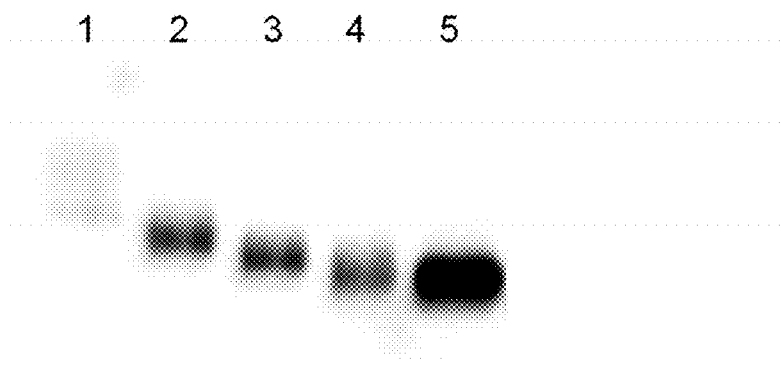

About 10 μL each of the culture supernatants of the GBA expressing cells and the GBA/AcGlcNAcase-3 expressing cells were subjected to SDS-PAGE electrophoresis (10% gel), and after completion of the run, transferred onto a nitrocellulose membrane. GBA transferred onto the nitrocellulose membrane was detected using a rabbit anti-human GBA antibody as the primary antibody and a labeled anti-rabbit IgG antibody as the secondary antibody. Comparison was made between the patterns of electrophoretic migration of GBA contained in the culture supernatant of the GBA expressing cells and the GBA/AcGlcNAcase-3 expressing cells, which revealed an increase in the migration distance corresponding to a lowered molecular weight of the latter as compared with the former (FIG. 3, lanes 1 and 5). As the structure of the sugar chain of the GBA contained in the culture supernatant of the GBA expressing cells was thought to be that of a complex-type sugar chain which has sialic acid residues at their non-reducing ends, sialidase (New England Biolabs), β1,4-galactosidase (New England Biolabs), and β-N-acetylglucosaminidase (New England Biolabs) were added in sequence. As a result, increase in migration distance in electrophoresis corresponding to lowered molecular weight was observed as each of these enzymes was added to the culture supernatant one by one (FIG. 3, lanes 2-4). Sialidase, β1,4-galactosidase, and β-N-acetylglucosaminidase have activities to remove sialic acid, galactose, and N-acetylgalactosamine, respectively, from non-reducing ends of sugar chains. Therefore, the result indicates that the structure of the sugar chain of GBA contained in the culture supernatant of the GBA expressing cells was that of a complex-type sugar chain. And the band of GBA treated with β-N-acetylglucosaminidase (FIG. 3, lane 4) exhibits a pattern of electrophoretic migration of GBA having a sugar chain whose non-reducing ends had been altered to mannose residues. Comparison of this band of the GBA which had been treated with β-N-acetylglucosaminidase (FIG. 3, lane 4) and the band of the GBA contained in the culture supernatant of the GBA/AcGlcNAcase-3 expression cells (FIG. 3, lane 5) shows that they exhibited approximately the same migration patterns. The result suggests that the sugar chain of the GBA expressed in the GBA/AcGlcNAcase-3 expressing cells was not a complex-type sugar chain having sialic acids at their non-reducing ends, but a sugar chain that had mannose residues at its non-reducing ends. Thus the result indicates that the non-mammalian, insect-originating β-N-acetylglucosaminidase 3 introduced into mammalian cells exhibits its activity in Golgi bodies and functions as an enzyme that removes N-acetylgalactosamine residues at the non-reducing ends, thereby turning the non-reducing ends of the sugar chain to mannose residues, during the process of glycosylation of GBA. There has been no report that non-mammalian, insect-originating β-N-acetylglucosaminidase 3 also functions in mammalian cells like this.

[Purification of Glucocerebrosidase—1st Process (Reverse-Phase Column Chromatography)]

The GBA expressing cells and the GBA/AcGlcNAcase-3 expressing cells were separately cultured, and glucocerebrosidase was purified from each of the cultures according to the following procedure. First, the culture supernatant was collected by centrifugation of the culture. To the culture supernatant, after filtered through a membrane filter, were added ethylene glycol, 1 M DTT, and 250 mM sodium acetate (pH 4.8) so that their final concentrations were 20% for ethylene glycol, 5 mM for DTT, and 50 mM sodium acetate. After application of the culture supernatant to a HITRAP PHENYL SEPHAROSE FF 5 mL column (GE Healthcare) equilibrated with a binding buffer [50 mM sodium acetate (pH 4.8), 20% ethylene glycol], the column was washed with 10 column volumes of the binding buffer. Then, glucocerebrosidase was eluted with 6 column volumes of an eluant given a linear gradient in which the mixing ratio of the binding buffer/elusion buffer [50 mM sodium acetate (pH 4.8), 20% ethylene glycol, 50% ethanol] was changed from 100/0 to 0/100. The activity of the fractions of the eluate was measured by the method described below, and GBA active fractions were collected. Flow rate was set at 1.5 mL/min in all the cases.

[Purification of Glucocerebrosidase—2nd Process (Cation-Exchange Column Chromatography)]

The fractions collected above in the 1st process was diluted by addition of an equal volume of purified water, and to this were further added ethylene glycol, 1 M DTT, and 250 mM sodium acetate (pH 4.8) so that their final concentrations were 20% for ethylene glycol, 5 mM for DTT, and 50 mM for sodium acetate. After application of the above fractions to a HITRAP CM SEPHAROSE FF 1 mL column (GE Healthcare) equilibrated with a washing buffer [30 mM sodium acetate (pH 5.6), 0.01% TWEEN 80], the column was washed with 10 column volumes (10 mL) of the washing buffer. Then, glucocerebrosidase was eluted with 8 column volumes of an eluant given a linear gradient in which the mixing ration of buffer A [50 mM citric acid, 0.01% TWEEN 80]/buffer B [50 mM sodium citrate, 0.01% TWEEN 80] was changed from 75:25 to 4:96, and then with 5 column volumes of an eluant in which the mixing ration of buffer A/buffer B was fixed to 4:96. The eluate was collected 1 mL each and to this 1 M mannitol was admixed. GBA activity of each fraction was measured by a method described below, and GBA active fractions were collected. Flow rate was set at 1.5 mL/min in all the cases.

[Measurement of GBA Activity]

GBA activity was measured with reference to the method described in Pasmanik-Chor M. et al., Biochem J 317, 81-88 (1996). Namely, 4-methylumbelliferyl phosphate (4-MUF, Sigma Chemical Co.) was dissolved in a dilution buffer [100 mM potassium phosphate buffer containing 0.125% Na-taurocholate, 0.15% TRITON X-100, and 0.1% bovine serum albumin (pH 5.96)], and diluted stepwise to prepare standard solutions with its concentrations adjusted to 200, 100, 50, 25, 12.5, 6.25, and 3.125 mM. A substrate solution was prepared by dissolving 4-methylumbelliferyl-β-D-glucopyranoside (Sigma Chemical Co.) at a concentration of 4 mM. Samples were diluted, if needed, with the dilution buffer before measurement. Ten μL each of the 4-MUF standard solutions or a sample was added to a fluoroplate F96, and then 70 μL of the substrate solution was admixed. After reaction was allowed to proceed for one hour at 37° C., 200 pt of 50 mM glycine-NaOH buffer (pH 10.6) was added to each well as a reaction terminating solution, and the intensity of fluorescence was measured using fluoroplate reader under the condition of excitation at wavelength of 355 nm and detection at wavelength of 460 nm. A standard curve was produced based on the intensity of fluorescence from the 4-MUF standard solutions, and the activity (nmol/h/mL) of each sample was calculated by interpolating its fluorescence intensity into the standard curve. Measurement was carried out in duplicate and their mean value was taken as the value measured.

[Measurement of Amount of Cellular Uptake of GBA Using a Macrophage Cell Line NR8383]

Measurement of the amount of cellular uptake of GBA using macrophage cell line NR8383 was performed with reference to the method described in Zhu Y. et al., J Pharmacol Exp Ther. 308, 705-11 (2004). NR8383 cells (rat alveolar macrophage-derived cell line, ATCC No. CRL-2192) were cultured in Kaighn's modification of Ham's F12 medium (F12K) containing 15% fetal bovine serum (FBS) (Invitrogen). When the NR8383 cells became confluent, the medium was replaced with a F12K containing 32 μM Conduritol B Epoxide (CBE) (Calbiochem), and culture was continued overnight (not longer than 18 hours) to deactivate the intrinsic GBA of NR8383 cells. The cells were collected by centrifugation, washed three times with F12K medium containing 15% FBS, then suspended in 20 mL of a measurement medium (F12K medium containing 25 mM HEPES, pH 6.8, and 4 mg/mL fetal bovine serum), and cultured for 2.5 hours in a $CO_2$ incubator. The cells were divided into two parts, and centrifuged and collected, and one part of the cells was resuspended in 5 mL of the measurement medium, and the other in 5 mL of the measurement medium which was supplemented with 50 mg/mL mannose. The density of the cells here was adjusted to $1\times10^7$ cells/mL, in both cases. These cell suspensions were dispensed into culture tubes by 190 μL each, and to them was admixed 10 μL each of the GBA sample so that predetermined final concentrations (mU/mL) of GBA were achieved, and shaking culture was performed for 2 hours at 37° C. A control was prepared by adding 10 μL of the measurement medium, instead of a GBA sample. After culture, the cells were collected by centrifugation, and washed three times with PBS containing 1 mg/mL mannan (Nacalai Tesque). Following further washing two times with PBS, the cells were lysed in 150 μL of a cell lysation solution [50 mM potassium phosphate, pH 6.5, 0.25% TRITON X-100, 1×protease inhibitor cocktail (Roche)]. The GBA activity in the cell lysates thus obtained was measured according to the above-described method for GBA measurement. The amount of GBA taken up by the macrophage cells was determined as the value derived by subtracting the GBA activity measured with the cells cultured in the mannose-containing measurement medium from the GBA activity measured with the cells cultured in the measurement medium not containing mannose. As a result, it was revealed that the GBA obtained in the culture supernatant of the GBA expressing cells was hardly taken up by the NR8383 cells, whereas the GBA obtained in the culture supernatant of the GBA/AcGlcNAcase-3 expressing cells was taken up by the NR8383 cells.

Figure 4:
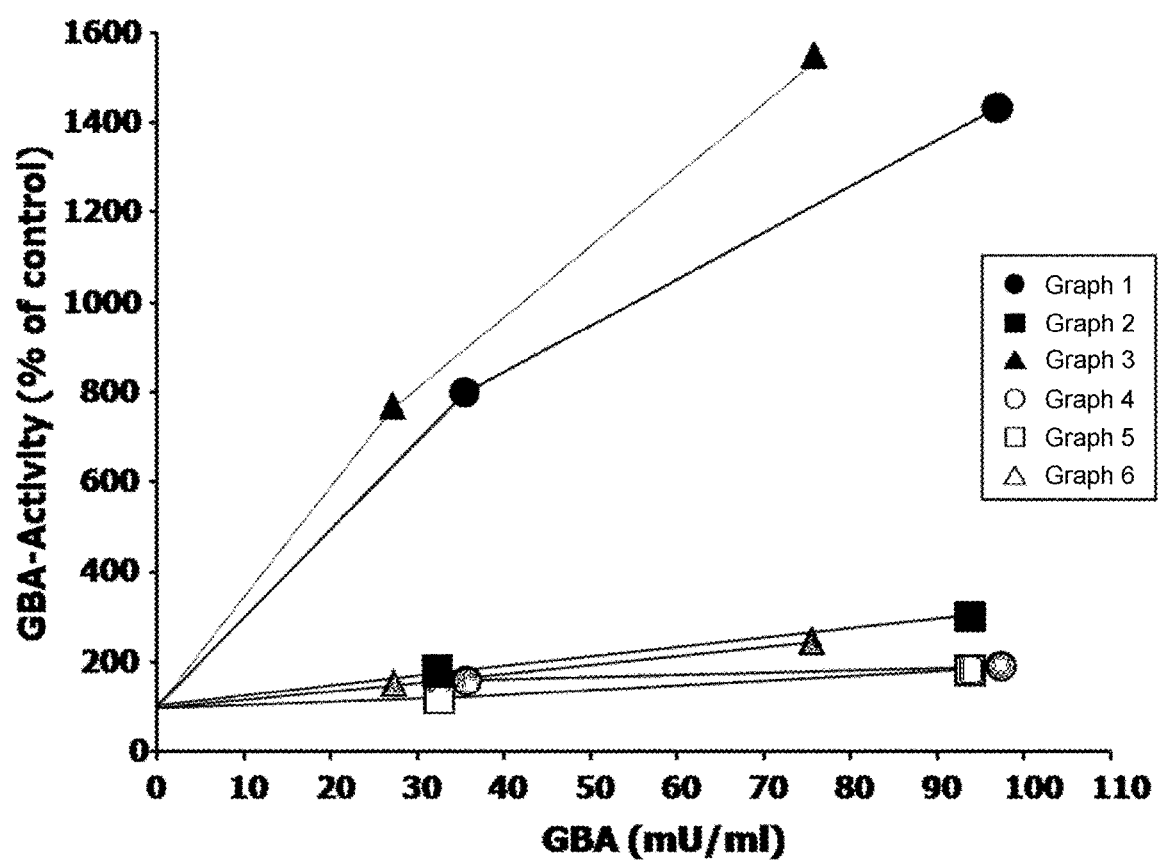
FIG. 4 A figure showing the results of measurement of the amount of cellular uptake by macrophages of glucocerebrosidase (GBA) obtained from GBA/AcGlcNAcase-3 expressing cells. Graph 1 shows cellular uptake of GBA obtained from GBA/AcGlcNAcase-3 expressing cells, Graph 2 of GBA obtained from GBA expressing cells, and Graph 3 of GBA obtained from GBA expressing cells and subjected to trimming of its sugar chains with enzymes, respectively. Graphs 4-6 show cellular uptake, in the presence of mannan, of GBA obtained from GBA/AcGlcNAcase-3 expressing cells, GBA obtained GBA expressing cells, and GBA obtained from GBA expressing cells and subjected to trimming of its sugar chains with enzymes, respectively. The vertical axis shows the amount of GBA taken up by the cells (% of control), and the horizontal axis the concentration of GBA (mU/mL), respectively.

The amount of GBA taken up by the macrophage cells was expressed in its ratio to the control, taking the GBA activity with the control for 100% (i.e., % of the control). As a result, it was revealed that the GBA obtained in the culture supernatant of the GBA expressing cells was hardly taken up by the macrophage cells (FIG. 4: Graph 2), whereas the GBA obtained in the culture supernatant of the GBA/AcGlcNAcase-3 expressing cells was taken up by the macrophage cells (FIG. 4: Graph 1). The GBA obtained in the culture supernatant of the GBA expressing cells and then altered so as to have mannose residues at the non-reducing ends of its sugar chains by treating it with sialidase (New England Biolabs), β1, 4-galactosidase (New England Biolabs), and β-N-acetylglucosaminidase (New England Biolabs), in sequence, was also taken up by the macrophage cells, as was the GBA obtained in the culture supernatant of the GBA/AcGlcNAcase-3 cells (FIG. 4: Graph 3). In the presence of mannose, GBA uptake by the macrophage was inhibited (FIG. 4: Graphs 4-6).

The above results demonstrate that the GBA expressed in the GBA/AcGlcNAcase-3 expressing cells has mannose residues at the non-reducing ends of its sugar chains and is efficiently taken up by macrophage cells via mannose receptors on their cell membrane.

[Construction of SfFDL and BmFDL Expressing Plasmids]

SfFDL gene originating from *Spodoptera frugiperda* and BmFDL gene originating from *Bombyx mori* were chemically synthesized, in which their respective codons were optimized for CHO cells.

The nucleotide sequence of SfFDL gene is set forth as SEQ ID NO:9 and the amino acid sequence encoded by it as SEQ ID NO:10, respectively. In the nucleotide sequence set forth as SEQ ID NO:9, nucleotides 1-6 corresponds to a MluI site, nucleotides 14-1909 to the SfFDL coding sequence, nucleotides 1910-1917 to a NotI site. Here, the amino acid sequence set forth as SEQ ID NO:10 is the amino acid sequence corresponding to the coding region of the nucleotide sequence set forth as SEQ ID NO:9, and is identical to the amino acid sequence encoded by the native SfFDL gene.

The nucleotide sequence of the BmFDL gene is set forth as SEQ ID NO:11, and the amino acid sequence encoded by it as SEQ ID NO:12, respectively. In the nucleotide sequence set forth as SEQ ID NO:11, nucleotides 1-6 corresponds to a MluI site, nucleotides 14-1909 to the BmFDL coding sequence, nucleotides 1910-1917 to a NotI site. Here, the amino acid sequence set forth as SEQ ID NO:12 is the amino acid sequence corresponding to the coding region of the nucleotide sequence set forth as SEQ ID NO:11, and identical to the amino acid sequence encoded by the native BmFDL gene.

Each of the above genes was digested with MluI and NotI, and incorporated into a pUC57 vector which had been digested with MluI and NotI. Then, the SfFDL gene and the BmFDL gene were cut out from the corresponding pUC57 vector with MluI and NotI, and severally incorporated into the expression vector pE-hygr constructed above, between its MluI and NotI sites. The pE-hygr with the incorporated SfFDL gene was designated SfFDL gene expression plasmid (pE-hygr(Sf-FDL)), and the pE-hygr with the incorporated BmFDL gene was designated BmFDL gene expression plasmid (pE-hygr(Bm-FDL)).

[Introduction of SfFDL and BmFDL Genes into GBA Expressing Cells]

Into the GBA expressing cells was separately introduced either pE-hygr(Sf-FDL) or pE-hygr(Bm-FDL) by electroporation, and the cells were subjected to a selective culture in CD Opti CHO medium containing 200 μM hygromycin and 500 μg/mL G418, to provide GBA expression cells separately transformed with the SfFDL gene and the BmFDL gene.

[Selective Culture by Kidney Bean Lectin (PHA-L4 and PHA-E4)]

The transformant cells obtained by the above selective culture were cultured in CD Opti CH medium containing 12 μg/mL PHA-L4 (J Oil Mills) and 12 μg/mL PHA-E4 (J Oil Mills) to annihilate complex type sugar-expressing cells among the above transformed cells and make them aggregate, and non-aggregated cells were collected. The collected non-aggregated cells were designated GBA/Sf-FDL expression cells for those transformed with the SfFDL gene, and GBA/Bm-FDL expressing cells for those transformed with the BmFDL gene.

[Analysis of Sugar Chain Structure by SDS-PAGE]

Ten μL each of the culture supernatants of the GBA expressing cells, GBA/AcGlcNAcase-3 expressing cells, GBA/Sf-FDL expressing cells, and GBA/Bm-FDL expressing cells were subjected to SDS-PAGE (10% gel), and after completion of the run, the protein was stained with SIMPLY BLUE Safe Stain (Invitrogen). In addition, the culture supernatants of the cells transformed with GBA/AcGlcNAcase-3 gene, the cells transformed with GBA/Sf-FDL gene, and the cells transformed with GBA/Bm-FDL gene, all before treatment with kidney bean lectin, were also subjected to SDA-PAGE under the same condition.

Figure 5:
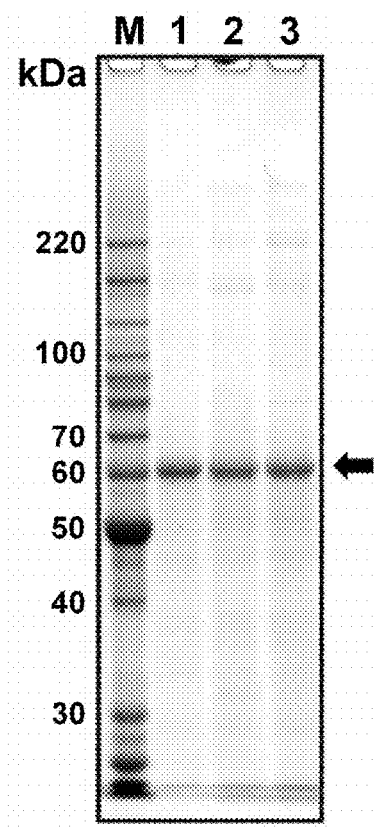
FIG. 5 A figure showing the pattern of electrophoresis migration of glucocerebrosidase (GBA) obtained from GBA/AcGlcNAcase-3 expressing cells. The arrowhead indicates the band corresponding to GBA. (lane M was loaded with molecular weight marker, lane 1 supernatant of the culture of GBA expressing cells, lane 2 supernatant of the culture of GBA/Sf-FDL expressing cells, lane 3 supernatant of the culture of GBA/Bm-FDL expressing cells, respectively)

Comparison of the migration patterns of the GBAs revealed that the GBAs contained in the culture supernatants of the GBA/Sf-FDL expressing cells and the GBA/Bm-FDL expressing cells were identical with that of the GBA/AcGlcNAcase-3 expressing cells (FIG. 5). Further, the migration pattern of the GBA contained in the cells transformed with the GBA/Sf-FDL gene and that of the cells transformed with the GBA/Bm-FDL gene, both before treatment with kidney bean lectin, also were partly identical with that of the GBA/AcGlcNAcase-3 expressing cells (data not shown). The results indicate that the GBAs expressed in the GBA/Sf-FDL expressing cells and the GBA/Bm-FDL expressing cells are those having mannose residues at the non-reducing ends of their sugar chains as are the GBA expressed in the GBA/AcGlcNAcase-3 cells. Further, the results indicates that SfFDL originating from *Spodoptera frugiperda* and BmFDL originating from *Bombyx mori* introduced into mammalian cells exhibit their activity in Golgi bodies and function as enzymes that remove, in the modification process of sugar chains of GBA, N-acetylgalactosamine residues occurring at the non-reducing ends of the sugar chains to alter the non-reducing ends to mannose residues, as does the β-N-acetylglucosaminidase 3. Thus the results indicate that SfFDL and BmFDL introduced and expressed in mammalian cells localize at the proper position of Golgi bodies and exhibit their activity therein.

[Measurement of Amount of Cellular Uptake of Glucocerebrosidase Obtained from Culture Supernatants of GBA/Sf-FDL Expressing Cells and GBA/Bm-FDL Expressing Cells]

Figure 6:
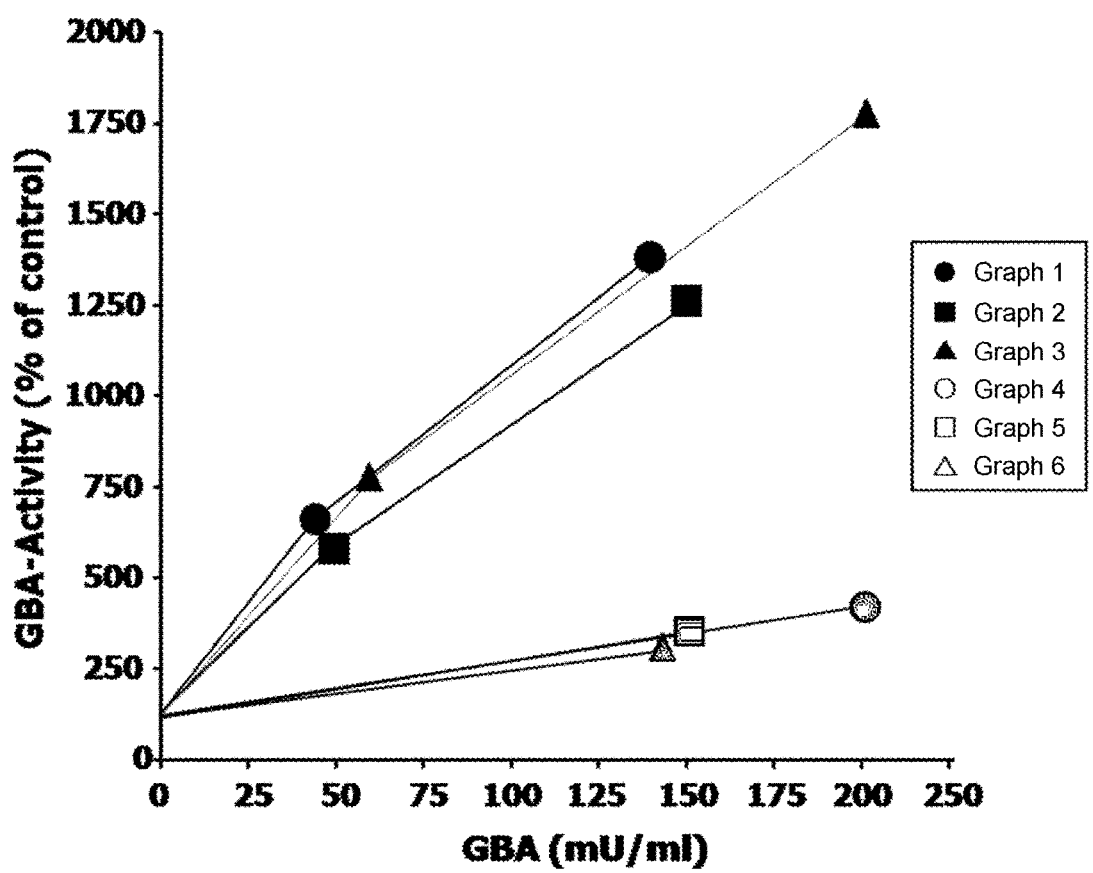
FIG. 6 A figure showing the result of measurement of the amount of cellular uptake of glucocerebrosidase (GBA) obtained from the supernatant of the culture of GBA/Sf-FDL expressing cells and GBA/Bm-FDL expressing cells. Graph 1 shows the amount or cellular uptake of GBA obtained from GBA/Sf-FDL expressing cells, Graph 2 GBA obtained from GBA/Bm-FDL expressing cells, Graph 3 GBA obtained from GBA/AcGlcNAcase-3 expressing cells, respectively. Graphs 4-6 show the amount of cellular uptake of GBA obtained from GBA/AcGlcNAcase-3 expressing cells, GBA obtained from GBA/Sf-FDL expressing cells, and GBA obtained from GBA/Bm-FDL expressing cells, respectively, in the presence of mannan. The vertical axis indicates the amount of GBA taken up by cells (% of control), and horizontal axis the GBA concentration (mU/mL), respectively.

GBA was purified from the respective culture media of the GBA/Sf-FDL expressing cells and the GBA/Bm-FDL expressing cells by the purification method consisting of the above-described first and second processes. With the GBAs thus purified, amount of their cellular uptake was measured using a macrophage cell line NR8383 by the method described above. As shown in FIG. 6, it was revealed that the GBA obtained from the culture supernatants of the GBA/Sf-FDL cells (Graph 1) and from the culture supernatant of the GBA/AcGlcNAcase-3 expressing cells (Graph 2) were taken up by the NR8383 cells at nearly the same level as the GBA obtained from the culture supernatant of the GBA/AcGlcNAcase-3 cells (Graph 3). Further, the efficacy of their cellular uptake was inhibited when mannan was added to the medium (Graphs 4-6). These results indicate that the GBAs expressed in the GBA/Sf-FD expressing cells and the GBA/Bm-FDL expressing cells have mannose residues at the non-reducing ends of their sugar chains and are efficiently taken up by macrophage cells via mannose receptors on their cell membrane, as does the GBA expressed in the GBA/AcGlcNAcase-3 expressing cells.

INDUSTRIAL APPLICABILITY

According to the present invention, recombinant glycoproteins having mannose residues at the end of its N-glycosidic bond-linked sugar chains can be provided using mammalian cells. Therefore, it enables one to easily and efficiently produce enzymes used, e.g., in enzyme replacement therapy of lysosomal storage diseases.

SEQUENCE LISTING FREE TEXT

SEQ ID NO:1: Primer Hyg-Sfi
SEQ ID NO:2: Primer Hyg-BstX
SEQ ID NO:3: Primer GBA-Mlu
SEQ ID NO:4: Primer GBA-Not
SEQ ID NO:5: Primer N-AGase5'-Sal
SEQ ID NO:6: Primer N-AGase5'-Mlu
SEQ ID NO:7: Primer N-AGase3'-Mlu
SEQ ID NO:8: Primer N-AGase3'-Not
SEQ ID NO:9: Artificial Sequence containing SfFDL CDS, bases 1-6: MluI site, bases 14-1909: CDS for SfFDL, bases 1910-1917: NotI site
SEQ ID NO:10: Synthetic Construct
SEQ ID NO:11: Artificial Sequence containing BmFDL CDS, bases 1-6: MluI site, bases 14-1909 CDS for BmFDL, bases 1910-1917: NotI site

SEQUENCE LISTING

GP149-PCT ST25

The invention claimed is:

1. A transformant mammalian cell producing a predetermined glycoprotein, the cell having an exogenous β-N-acetylglucosaminidase gene of insect origin introduced and allowed to express itself therein and having an exogenous gene encoding the predetermined glycoprotein further introduced and allowed to express itself.

2. The transformant mammalian cell according to claim 1, wherein β-N-acetylglucosaminidase expressed following introduction of the β-N-acetylglucosaminidase gene exhibits the activity thereof in Golgi bodies.

3. The transformant mammalian cell according to claim 2, wherein the insect is an insect of Lepidoptera.

4. The transformant mammalian cell according to claim 3, wherein the insect of Lepidoptera is *Spodoptera frugiperda* or *Bombyx mori*.

5. The transformant mammalian cell according to claim 4, wherein the β-N-acetylglucosaminidase gene is one or more genes selected from the group consisting of β-N-acetylglucosaminidase 1 gene, β-N-acetylglucosaminidase 3 gene, SfFDL gene, and BmFDL gene.

6. The transformant mammalian cell according to claim 5, wherein the exogenous gene encoding the predetermined glycoprotein is a gene of human origin.

7. The transformant mammalian cell according to claim 6, wherein the gene of human origin is a gene encoding a lysosomal enzyme.

8. The transformant mammalian cell according to claim 7, wherein the lysosomal enzyme is selected from the group consisting of glucocerebrosidase, acid sphingomyelinase, lysosomal acid lipase, acid α-glucosidase, N-acetylgalactosamine-4-sulfatase, iduronate-2-sulfatase, α-L-iduronidase, α-galactosidase A, hexosaminidase, α-N-acetylgalactosaminidase, α-mannosidase, and sialidase.

9. The transformant mammalian cell according to claim 7, wherein the lysosomal enzyme is glucocerebrosidase.

10. A method for production of a glycoprotein having N-glycosidic bond-linked sugar chains, wherein all or part of the non-reducing ends of the sugar chains comprise mannose residues, wherein the method comprises the steps of:
    (a) culturing the mammalian cell according to claim 1 in a medium to allow the glycoprotein be expressed, and
    (b) purifying the glycoprotein expressed in (a) above.

11. The method for production according to claim 10, wherein the exogenous gene encoding the glycoprotein is a gene of human origin.

12. The method for production according to claim 11, wherein the gene of human origin is a gene encoding a lysosomal enzyme.

13. The method for production according to claim 12, wherein the lysosomal enzyme is selected from the group consisting of glucocerebrosidase, acid sphingomyelinase, lysosomal acid lipase, acid α-glucosidase, N-acetylgalactosamine-4-sulfatase, iduronate-2-sulfatase, α-L-iduronidase, α-galactosidase A, hexosaminidase, α-N-acetylgalactosaminidase, α-mannosidase, and sialidase.

14. The method for production according to claim 12, wherein the lysosomal enzyme is glucocerebrosidase.

* * * * *